(12) United States Patent
Takagi et al.

(10) Patent No.: US 7,547,540 B2
(45) Date of Patent: Jun. 16, 2009

(54) CELL/TISSUE CULTURE APPARATUS

(75) Inventors: Takao Takagi, Fuji (JP); Setsuo Watanabe, Fuji (JP)

(73) Assignee: Takagi Industrial Co., Ltd., Shizuoka-ken (JP)

( * ) Notice: Subject to any disclaimer, the term of this patent is extended or adjusted under 35 U.S.C. 154(b) by 733 days.

(21) Appl. No.: 10/487,455

(22) PCT Filed: Aug. 29, 2002

(86) PCT No.: PCT/JP02/08753
§ 371 (c)(1),
(2), (4) Date: Feb. 24, 2004

(87) PCT Pub. No.: WO03/029398
PCT Pub. Date: Apr. 10, 2003

(65) Prior Publication Data
US 2004/0235153 A1 Nov. 25, 2004

(30) Foreign Application Priority Data
Aug. 30, 2001 (JP) .............................. 2001-261556

(51) Int. Cl.
*C12M 1/00* (2006.01)
(52) U.S. Cl. .............. 435/289.1; 435/293.1; 435/302.1; 623/915; 623/920
(58) Field of Classification Search .............. 435/289.1, 435/293.1, 302.1; 623/915, 920; 73/796, 73/797
See application file for complete search history.

(56) References Cited

U.S. PATENT DOCUMENTS 4,195,563 A * 4/1980 Budraitis et al. .............. 100/99

(Continued)

FOREIGN PATENT DOCUMENTS

JP 63109348 A * 5/1988

(Continued)

OTHER PUBLICATIONS

Liu et al. 'Bio-Stretch, A computerized cell strain apparatus for three-dimensional organotypic cultures.' In Vitro Cell. Dev. Biol.-Animal. vol. 35 (Feb. 1999), pp. 87-93.*

(Continued)

*Primary Examiner*—William H Beisner
(74) *Attorney, Agent, or Firm*—Connolly Bove Lodge & Hutz LLP

(57) ABSTRACT

A cell/tissue culture apparatus for applying a desired tensile stress to a material to be cultivated such as a cell or tissue as a physical stimulation, thereby enhancing acceleration of culture of the material to be cultivated. The cell/tissue culture apparatus comprises a chamber (a culture chamber 8) for circulating a culture fluid (24), a material to be cultivated (a matrix 32) that is placed and cultivated in the chamber, stress generation means (an electromagnetic stretcher 38, an actuator 56) for causing a tensile stress to act on the material to be cultivated from an outside of the chamber, and control means (controllers 50, 60) for causing the tensile stress generated by the stress generation means to intermit as well as undergo gradual increase or gradual decrease. The material to be cultivated can be caused to undergo expansion or contraction by applying and relieving the tensile stress, thereby applying a physical stimulation necessary for the proliferation to the material to be cultivated.

14 Claims, 23 Drawing Sheets

U.S. PATENT DOCUMENTS

| | | | | |
|---|---|---|---|---|
| 4,530,907 | A | * | 7/1985 | Peterson et al. ............... 435/32 |
| 4,940,853 | A | * | 7/1990 | Vandenburgh ............... 435/395 |
| 5,142,769 | A | * | 9/1992 | Gold et al. ................. 29/621.1 |
| 5,153,136 | A | | 10/1992 | Vandenburgh |
| 6,107,081 | A | * | 8/2000 | Feeback et al. ........... 435/284.1 |
| 6,114,164 | A | * | 9/2000 | Dennis et al. ............ 435/286.1 |
| 6,121,042 | A | | 9/2000 | Peterson et al. |

FOREIGN PATENT DOCUMENTS

| | | |
|---|---|---|
| JP | 06-269274 | 9/1994 |
| JP | 09-313166 | 12/1997 |
| JP | 10-155475 | 6/1998 |
| JP | 11-504216 | 4/1999 |
| WO | WO-96-34090 | 10/1996 |
| WO | 9945097 | 9/1999 |

OTHER PUBLICATIONS

International Search Report dated Nov. 1, 2002, International Appl. No. PCT/JP02/08753, 3 pages.

Supplemental European search report issued in corresponding European Patent Application No. 02762902.1 dated Jul. 3, 2008.

* cited by examiner

F I G. 5
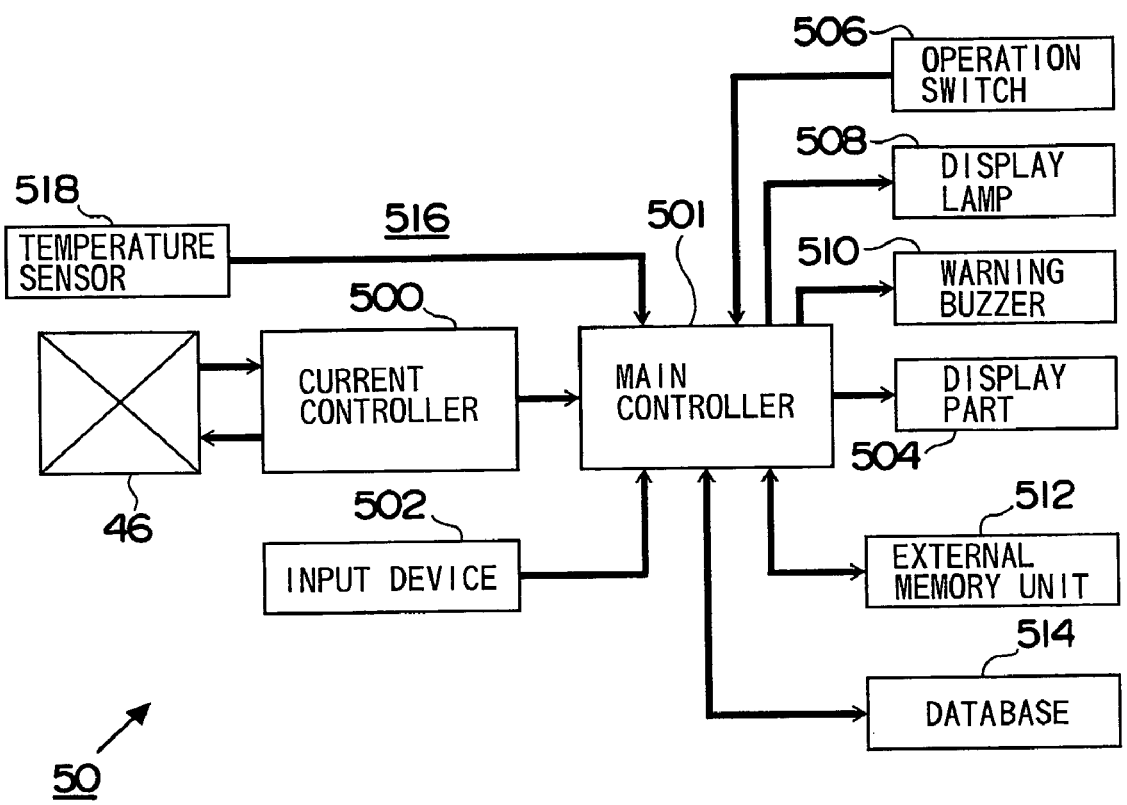

FIG. 20
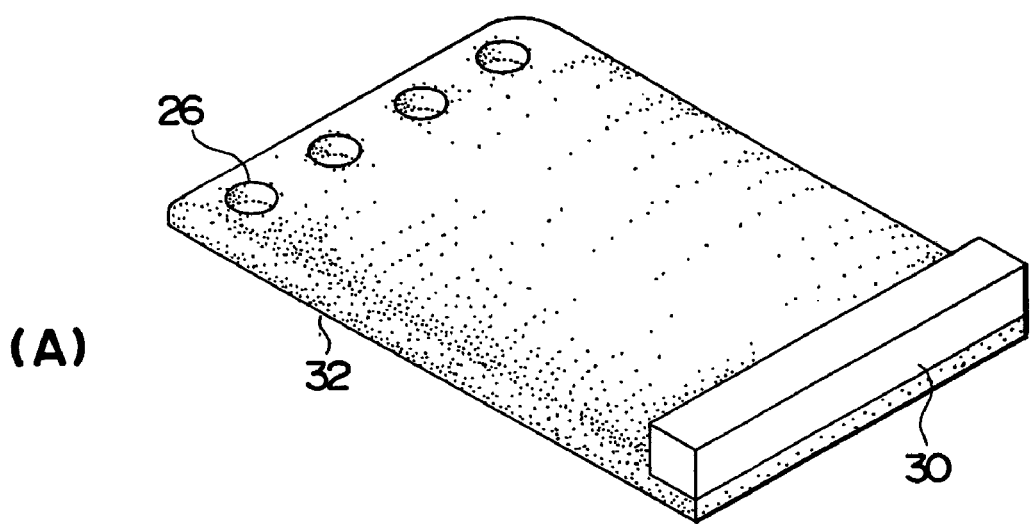
(A)
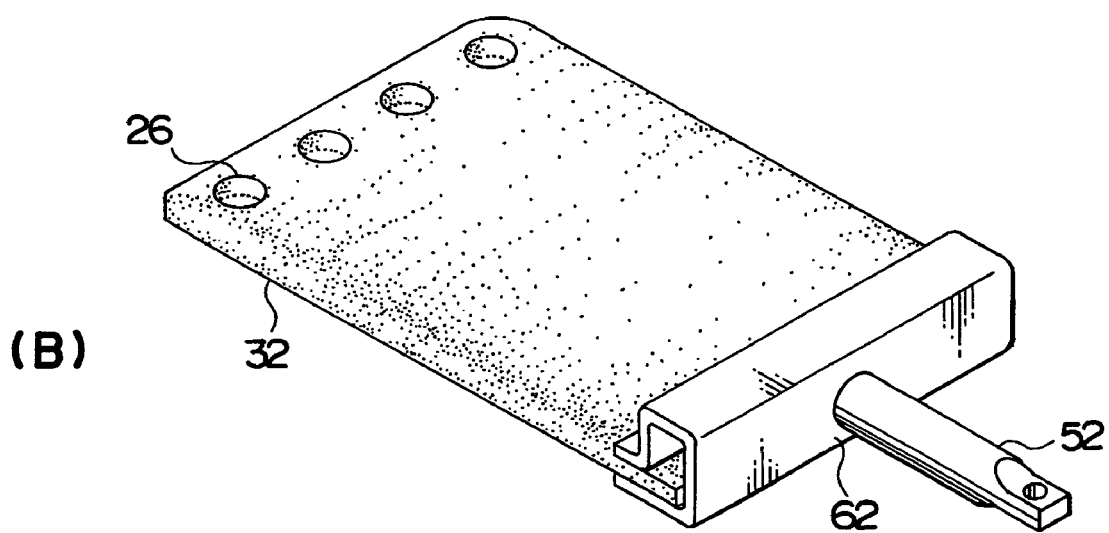
(B)

FIG. 21
(A)
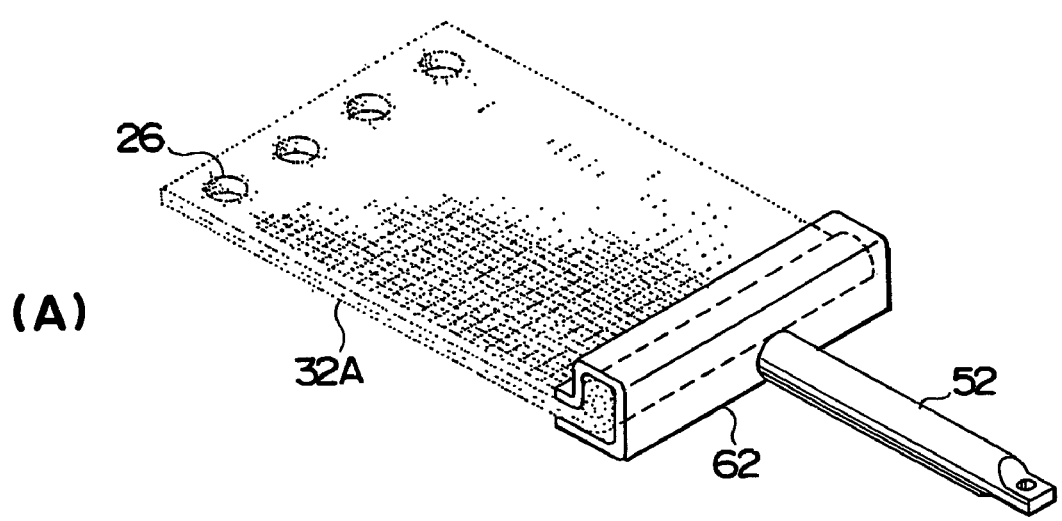
(B)
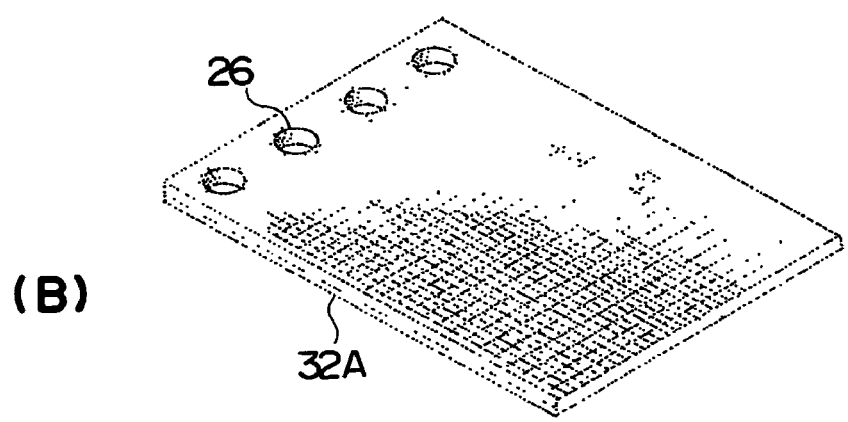

FIG. 23
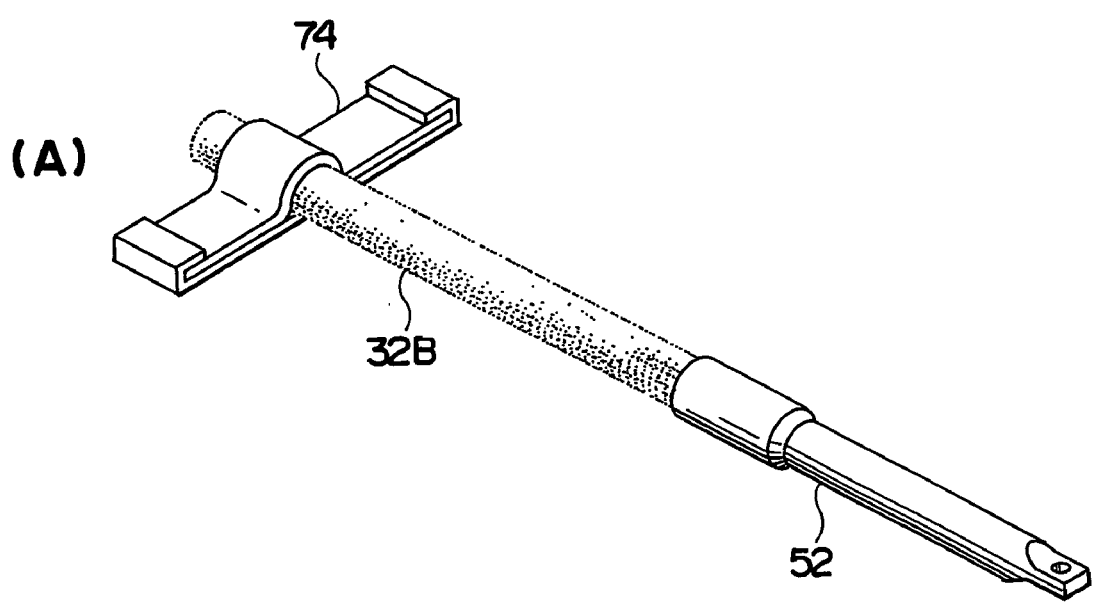
(A)
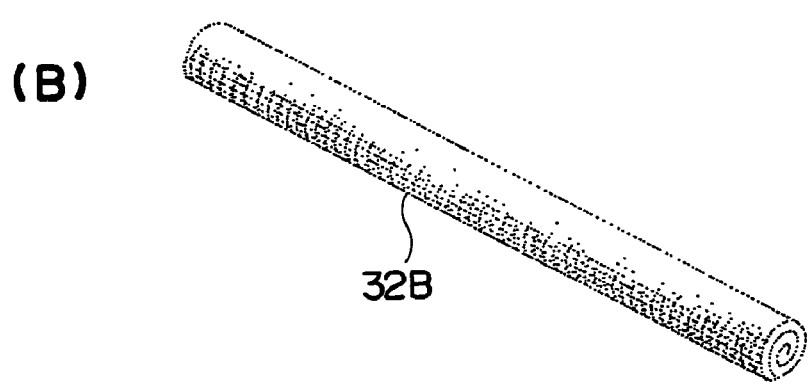
(B)

...

CELL/TISSUE CULTURE APPARATUS

TECHNICAL FIELD

The present invention relates to a cell/tissue culture apparatus for use in the culture of a cell or tissue, and so forth to which a tissue engineering is applied, more particularly, relates to a cell/tissue culture apparatus for efficiently realizing a metabolism function of a cell or tissue when performing an in vitro culture of the cell or tissue of a living body such as a human body, and so forth, and applying a physical stimulation necessary for prolongation, differentiation, and acceleration of a cell to a material to be cultivated.

BACKGROUND TECHNOLOGY

There has been conventionally employed a method of performing an in vitro culture of a cell or tissue of a living body such as a human body, and so forth, wherein a temperature, a humidity, a carbon dioxide concentration, an oxygen concentration in an incubator (culture housing) are maintained at proper conditions, and the cell is cultivated in the incubator. The cell or tissue is placed in a culture fluid in a suspending state, or it is fixed to an interior or a surface of a gel in which the culture fluid ingredient is contained, thereby proliferating and growing the cell or tissue, or the cell or tissue is transplanted in a material, that is exemplified as a matrix or a scaffold, a carrier or a mold, and so forth (hereinafter referred to as "matrix"), thereby proliferating and growing the cell or tissue.

Meanwhile, it is important to apply a physical stimulation to a cell or tissue to be cultivated in addition to an environment condition such as a temperature, a humidity, a carbon dioxide concentration, an oxygen concentration for proliferating and growing the cell or tissue. Such a physical stimulation is an indispensable constituent for facilitating differentiation and growth of the cell or tissue and for growing the cell or tissue to be rendered closer to the cell or tissue in the living body. For a technology for applying a physical stimulation to the cell or tissue for proliferating and growing the cell or tissue, there are, for example, Japanese Patent No. 3 163 533 entitled "An elastic stimulation application load apparatus for use in a cell to be cultivated using a silicone belt".

Although it is necessary to add a dynamic condition such as a physical stimulation to a static condition, a so-called culture environment such as a temperature, a humidity, a carbon dioxide concentration, an oxygen concentration for proliferating and growing the cell or tissue, there is a possibility that the control of the dynamic condition together with the static condition renders a control mode complex, and a factor caused by the invasion of various bacteria, and so forth increases. It is an important challenge to protect a material to be cultivated from contamination with various bacteria.

Accordingly, it is an object of the present invention to provide a cell/tissue culture apparatus for applying a desired tensile stress to a material to be cultivated such as a cell or tissue as a physical stimulation, thereby enhancing acceleration of culture of the material to be cultivated.

DISCLOSURE OF THE INVENTION

The cell/tissue culture apparatus according to the present invention comprises a chamber (a culture chamber 8) for circulating a culture fluid (24), a material to be cultivated (a matrix 32, culture materials 32A, 32B) that is placed and cultivated in the chamber, stress generation means (an electromagnetic stretcher 38, an actuator 56) for causing a tensile stress to act on the material to be cultivated from an outside of the chamber, and control means (controllers 50, 60) for causing the tensile stress generated by the stress generation means to intermit, and undergo gradual increase or gradual decrease in magnitude, wherein the tensile stress applied to the material to be cultivated is caused to intermit as well as undergo the gradual increase or gradual decrease in magnitude over time.

More specifically, the tensile stress generated by the stress generation means is applied to the material to be cultivated, placed in the chamber, from an outside of the chamber. And the stress is controlled by the control means in such a manner that it is caused to intermit or caused to render in a state of gradual increase or gradual decrease. As a result, the material to be cultivated expands when the tensile stress is applied and contracts when the tensile stress is relieved, thereby undergoing expansion and contraction. For example, by securely attaching one end of the material to be cultivated to an inner part of the chamber and causing tension to discontinuously act on the other end of the material to be cultivated, the material to be cultivated can be caused to undergo expansion or contraction, so that a tensile stress corresponding to the magnitude of the expansion or contraction, the magnitude of the tension, intermittence, and so forth is applied to the material to be cultivated, whereupon a physical stimulation necessary for proliferation thereof is applied to the material to be cultivated so that it is possible to create tenacious tissues such as ligaments, and so forth by cultivating the same. In this case, for the stress generation means for causing the tensile stress, it is possible to use means for generating mechanical force, such as a cylindrical device and so forth.

The cell/tissue culture apparatus according to the present invention may further comprises a chamber (a culture chamber 8) for circulating a culture fluid (24), an elastic member (a culture sheet 22) placed in the chamber, together with the material to be cultivated (the matrix 32, the culture material 32A, 32B), and stress generation means (the electromagnetic stretcher 38, the actuator 56) for causing a tensile stress to act on the material to be cultivated from an outside of the chamber through the intermediary of the elastic member and control means (controllers 50, 60) for intermitting the tensile stress generated by the stress generation means, and enabling the tensile stress to undergo gradual increase or gradual decrease in magnitude, wherein the tensile stress applied to the material to be cultivated is caused to intermit as well as undergo the gradual increase or gradual decrease in magnitude over time.

Incidentally, in causing tension to act directly on the material to be cultivated, it is important to give sufficient consideration to growth of the material to be cultivated so as to prevent damage or rupture from occurring thereto. Hence if the material to be cultivated is adhered to the elastic member, the material to be cultivated will be protected by the elastic member, and can undergo expansion or contraction together with the elastic member. By applying the tensile stress generated by the stress generation means to the elastic member to thereby cause the same to undergo expansion or contraction, it is possible to cause a tensile stress, corresponding to such expansion or contraction, to act on the material to be cultivated. If the material to be cultivated is cultivated by causing such a tensile stress to act thereon, this will lead to realize a cell or tissue such as tendons, ligaments, and so forth to which a tensile stress is incessantly applied. For example, by securely attaching one end of the elastic member in which the material to be cultivated is transplanted to an interior of the chamber and causing tension to discontinuously act on the other end of the elastic member, the elastic member can be caused to undergo expansion or contraction, so that a tensile stress corresponding to the magnitude of the expansion or contraction, the magnitude of the tension, intermittence of the tension, and so forth can be applied to the material to be cultivated.

With the cell/tissue culture apparatus according to the present invention, the stress generation means (the electromagnetic stretcher 38) is characterized in comprising an electromagnetic force generation unit for causing magnetic force to act on a magnetic body (30) attached to the material to be cultivated or the elastic member. That is, if electromagnetic force is caused to act on the magnetic body (30) attached to the material to be cultivated or the elastic member, a necessary tensile stress can be applied from an outside of the chamber, in which the material to be cultivated is placed, to the material to be cultivated or the elastic member by the magnetic force. In this case, because a tensile stress can be applied to the material to be cultivated without being in contact therewith and indirectly from an outside of the chamber, the material to be cultivated can be protected from contamination with various bacteria and so on.

With the cell/tissue culture apparatus according to the present invention, it is characterized in that for the elastic member, use is made of a silicone rubber sheet. That is, the silicone rubber sheet has elasticity necessary for applying tensile stress as physical stimulation to the material to be cultivated and does not contaminate the material to be cultivated.

Further, with the cell/tissue culture apparatus according to the present invention, it is characterized in that a culture unit (2) in which the chamber is formed is attachable to, and detachable from a culture circuit (circulation path 23) for circulating the culture fluid. That is, the material to be cultivated can be transferred along with the culture unit, and the culture unit is hermetically sealed with ease, so that the material to be cultivated can be protected from contamination with various bacteria, and so forth.

Still further, with the cell/tissue culture apparatus according to the present invention, it is characterized in that a part or whole of the culture unit in which the chamber is formed is rendered transparent, and may have photographing means (CCD camera 522) is provided, thereby enabling the material to be cultivated, placed in the chamber, to be photographed from an outside of the chamber. That is, the material to be cultivated in a culture state can be photographed, and culture conditions can be easily monitored without disturbing culture environments inside the chamber. Photographs thereof or image data thereof serve as important reference material concerning proliferation and growth of the material to be cultivated.

With the cell/tissue culture apparatus according to the present invention, it is characterized in that the material to be cultivated is formed in a flat sheet, and a cylindrical or prismatic shape. That is, the material to be cultivated is cultivated in the flat sheet, and the cylindrical or prismatic shape as a form corresponding to the portion of a human body such as ligaments and so forth to be repaired.

With the cell/tissue culture apparatus according to the present invention, it is characterized in that the material to be cultivated has a fibrous or string shaped tissue, woven therein, thereby having elasticity. That is, by weaving the fibrous or string shaped tissue, for example, the tissue made of collagen formed in fibrous shape or in string shape, it is possible to cause the tissue prior to proliferation to retain proper elasticity and tenacity, so that tenacious tissue, such as ligaments, and so forth can be cultivated.

Objects, features, advantages, and so forth of the present invention are more clarified by taking into account the description of the mode for carrying out the invention and the embodiments as illustrated in the drawings.

BRIEF DESCRIPTION OF THE DRAWINGS

FIG. 5 is a block diagram showing a controller.

FIG. 20 is a view showing another embodiment of a material to be cultivated.

FIG. 21 is a view showing still another embodiment of a material to be cultivated.

FIG. 23 is a view showing still another embodiment of a material to be cultivated.

BEST MODE FOR CARRYING OUT THE INVENTION

A mode for carrying out the present invention is now described in detail with reference to the embodiments.

Figure 1:
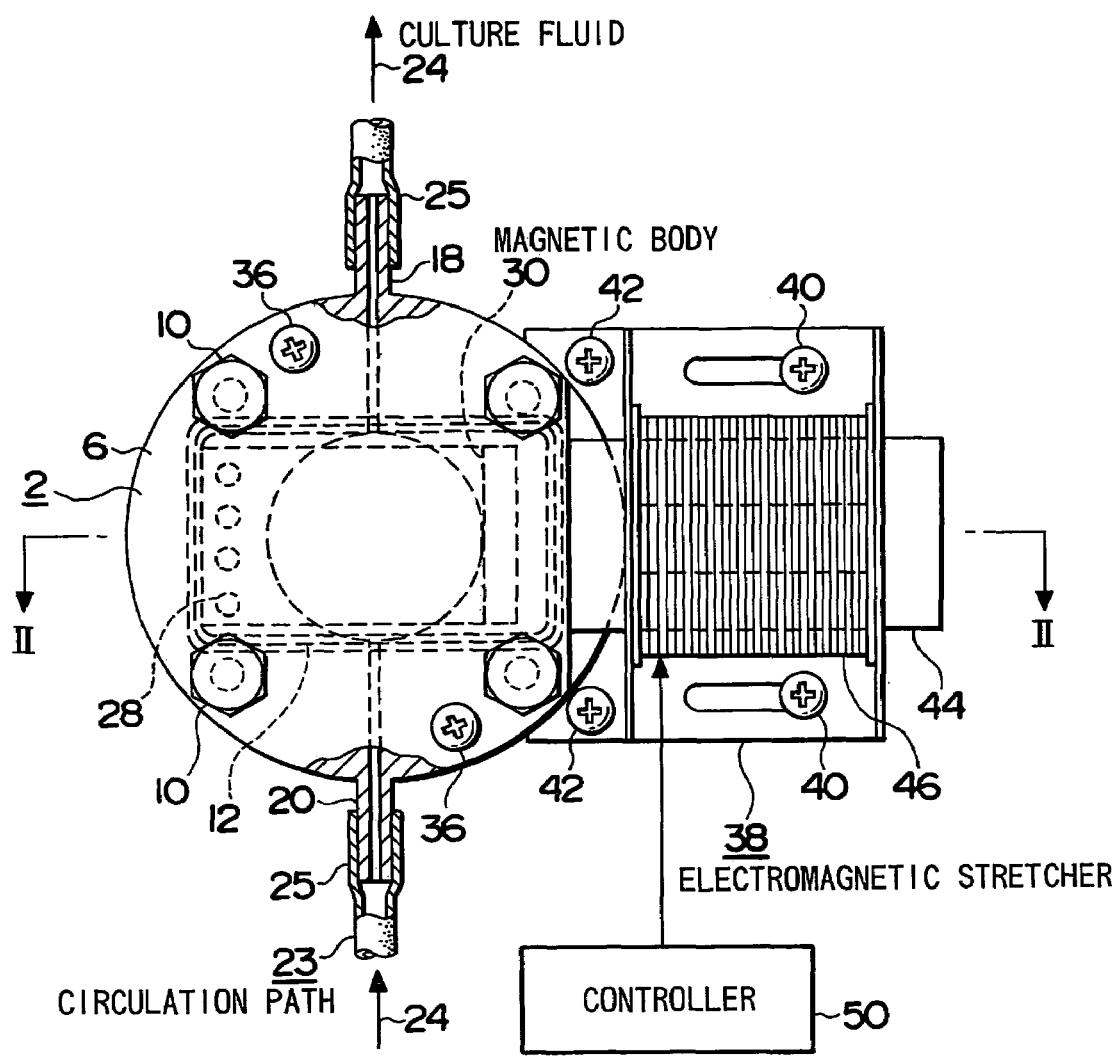
FIG. 1 is a front view showing a first embodiment of a cell/tissue culture apparatus according to the present invention.
Figure 2:
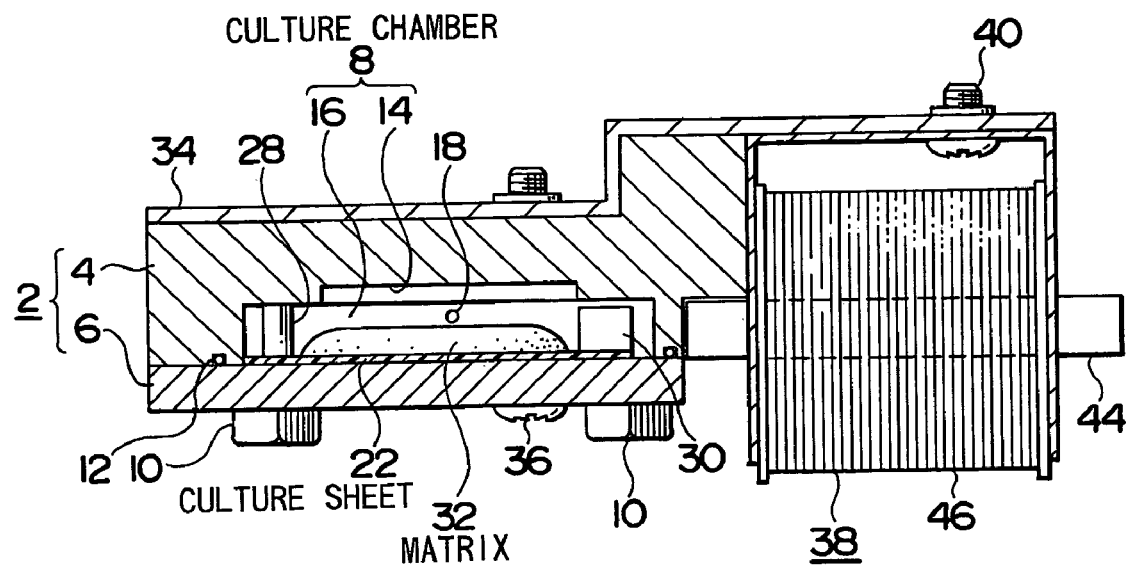
FIG. 2 is a sectional view taken along the line II-II in FIG. 1.
Figure 3:
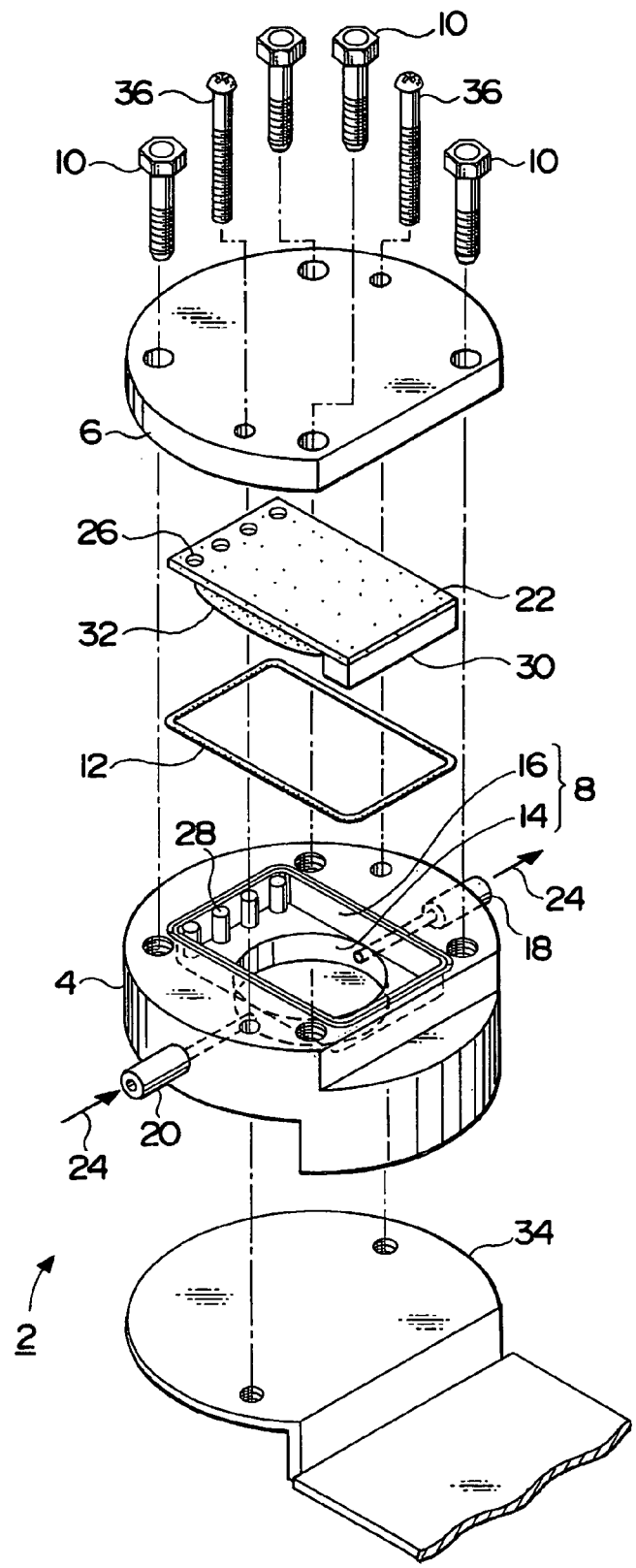
FIG. 3 is an exploded perspective view of a culture unit.
Figure 4:
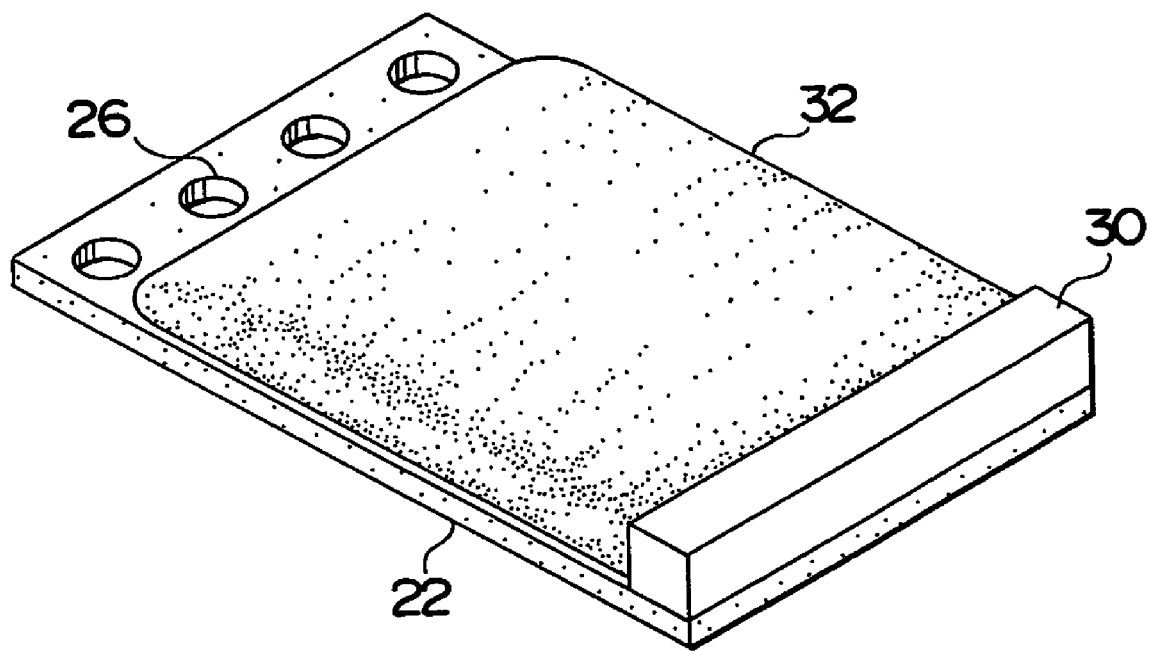
FIG. 4 is a perspective view showing a culture sheet.
Figure 6:
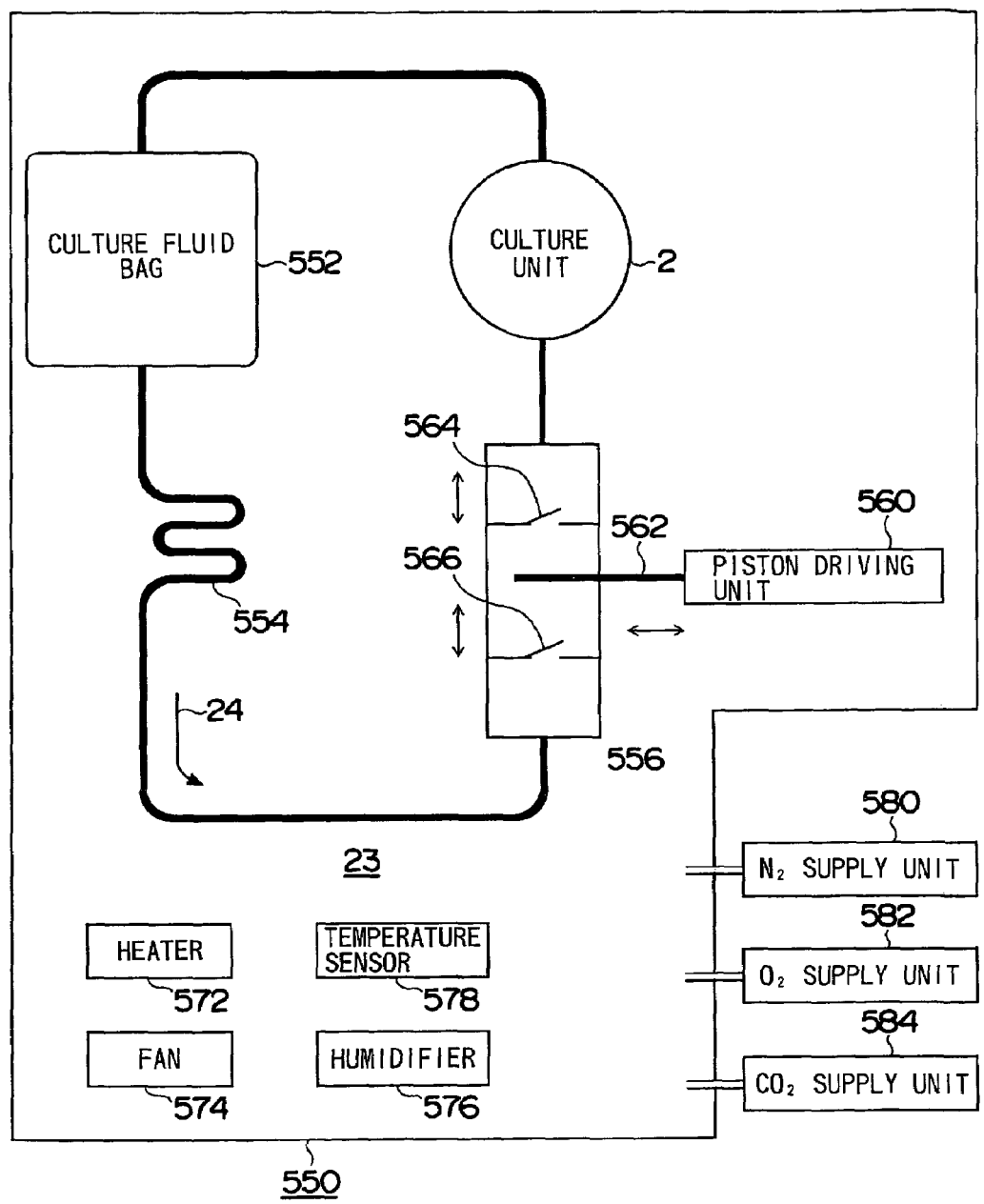
FIG. 6 is a view showing the culture unit installed in a culture housing.

FIGS. 1 to 6 show a first embodiment of a cell/tissue culture apparatus according to the present invention, wherein FIG. 1 shows configurations of a culture unit and a driving part, FIG. 2 is a sectional view taken along the line II-II in FIG. 1, FIG. 3 shows a configuration of a culture unit, FIG. 4 shows a culture sheet, FIG. 5 shows a controller and FIG. 6 shows a culture environment.

A culture unit 2 for forming a culture space in which a material to be cultivated serving as a cell or tissue of a living body of a human, and so forth is cultivated is provided in the cell/tissue culture apparatus. The culture unit 2 has a high grade heat resistant property and is made of a synthetic resin material or a metal material from which a material adversely affecting on a living body does not liquate out, for example, fluorine resin, PEEK, high grade heat resistance polypropylene, silicone, stainless steel, and so forth.

The culture unit 2 comprises a container 4 and a cover 6 which is detachably attached to the container 4, and a culture chamber 8 serving as a closed culture space is formed inside the container 4 hermetically sealed with the cover 6. According to this embodiment, the cover 6 is detachably fixed to the container 4 by a plurality of fixing bolts 10, and a rectangular O ring 12 is interposed between the container 4 and the cover 6 so as to enclose the a culture chamber 8, so that a sufficient hermeticity is held in the culture chamber 8. The container 4 may be configured to form a transparent part or made of a transparent material so as to visually confirm a culture state inside the container 4.

The culture chamber 8 has a circular part 14 at the inner side and a rectangular part 16 at the opening side, wherein circular port parts 18, 20 are formed on a wall part of the container 4 at the circular part 14 side in a direction of a diameter of the circular part 14, and a culture sheet 22 made of silicon rubber, and so forth serving as an elastic member forming a culture floor is installed at the rectangular part 16 side. Circulation tubes 25 of a circulation path 23 serving as a culture circuit are connected to the circular port parts 18, 20, and a culture fluid 24 which is supplied through the circulation path 23 is circulated and stayed inside the culture chamber 8.

The culture 22 is narrower than the rectangular part 16 of the culture chamber 8 and has a short rectangular shape, and a plurality of through holes 26 are formed at regular intervals in a width direction of the culture sheet 22 at one end side thereof, and a plurality of retaining projections 28 serving as fixing means, which are formed at the rectangular part 16 side of the culture chamber 8, are inserted into the respective through holes 26. One end of the culture sheet 22 is fixed to an interior of the culture chamber 8 by the engagement between the retaining projections 28 and the through holes 26. According to this embodiment, although the retaining projections 28 are formed in a columnar shape but they may be formed in a prismatic shape. A prismatic magnetic body 30 is attached to the other end of the culture sheet 22, namely, at the free end side of the culture sheet 22, and as shown in FIG. 4, a matrix 32 made of collagen sponge, and so forth is attached between the magnetic body 30 and the through holes 26 on the surface of the culture sheet 22. The matrix 32 is a material to be cultivated, for example, ligament cell, tendon cell, mussel cell, and so forth of a human are seeded in the matrix 32.

The container 4 and the cover part 6 of the culture unit 2 are integrated with each other and detachably attached to a base board 34 by fixing bolts 36. Further, an electromagnetic stretcher 38 serving as stress generating means for generating a stress by an electromagnetic force is fixed to the base board 34 by fixing bolts 40. The fixing bolts 42 are means for fixing the base board 34 to a base table, not shown. The base board 34 may be configured to form a transparent part corresponding to the culture chamber 8 or made of a transparent material so as to visually confirm a culture status inside the container 4.

The electromagnetic stretcher 38 is stress generating means for generating a stress by an electromagnetic force and is formed by solenoid 46 wound around a core 44 made of ferrite, and so forth, wherein one end of the core 44 is allowed to oppose the magnetic body 30 inside the culture chamber 8. A control unit 50 serving as control means for allowing a driving current to flow and canceling thereof, and so forth is connected to solenoid 46 of the electromagnetic stretcher 38.

A driving current is forced to flow in the solenoid 46 of the electromagnetic stretcher 38, and thereto.

With such an arrangement, when the solenoid 46 is energized to cause the electromagnetic force to act on the magnetic body 30 through the core 44, the magnetic body 30 is allowed to be attracted toward the core 44 so that a tension is caused to act on the matrix 32 serving as a cell or tissue which proliferates inside the collagen sponge together with the culture sheet 22 so as to expand the matrix 32. If the electromagnetic force is cancelled, the culture sheet 22 is contracted owing to its elasticity. As a result, a tensile stress and a recovery force caused by the expansion and contraction of the culture sheet 22 can be caused to act on the matrix 32. At this time, the supply and circulation of the culture fluid 24 which is needed for culture are effected through the circulation path 23 to enhance proliferation of the cell or tissue.

There are provided in the controller 50, for example, as shown in FIG. 5, a current controller 500 for allowing a driving current to flow to the solenoid 46 of the electromagnetic stretcher 38 and controlling the solenoid 46, and a main controller 501 for controlling the current controller 500, and effecting driving control, display control, and so forth, wherein the main controller 501 executes a program control for setting a tension pattern, and so forth. The main controller 501 has a CPU serving as a processing means, a ROM or a RAM serving as a memory, and so forth, and a program setting such as a rotation condition, and so forth is effected from an externally connected input unit 502. A display part 504, an operation switch 506 for issuing an operation command, operation display means, for example, a display lamp 508, a warning buzzer 510 serving as alarming means, an external memory unit 512, a data base 514, and so forth serving as means for storing various data are provided in the main controller 501, respectively. Further, a safety unit 516 for preventing anomalous operation is provided in the controller 50, and the safety unit 516 comprises a temperature sensor 518 provided in the solenoid 46 for detecting the increase of temperature of the solenoid 46, the current controller 500 serving as detecting means for detecting an excessive current flowing to the solenoid 46, and the main controller 501 for preventing anomalous operation based on an output of detection of the increase of temperature and the excessive current.

Further, according to the cell/tissue culture apparatus, it is configured, for example, as shown in FIG. 6, such that it is accommodated in a culture housing 550 forming an optimum culture environment. There are provided in the circulation path 23 a culture fluid bag 552 for storing the culture fluid 24 therein, a gas absorption tube 554 for allowing the circulation path 23 to absorb gas and a fluid supply unit 556 for effecting circulation of the culture fluid 24. A piston 562 which is moved back and forth by a piston driving unit 560 is provided in the fluid supply unit 556, wherein when the piston 562 is moved forward, a valve 564 is opened and a valve 566 is shut while when the piston 562 is moved backward, the valve 564 is shut and the valve 566 is opened, thereby effecting delivery of a predetermined amount of culture fluid 24.

The culture housing 550 has a heater 572 serving as heating means, a fan 574 serving as blowing means, a humidifier 576 serving as means for setting a humidity as desired, and a temperature sensor 578, and to which $N^2$ is supplied from an $N^2$ supply unit 580, $O^2$ is supplied from an $O^2$ supply unit 582, and $CO^2$ is supplied from a $CO^2$ supply unit 584, thereby forming an optimum culture environment adapted for the proliferation and growth of the cell or tissue.

Figure 7:
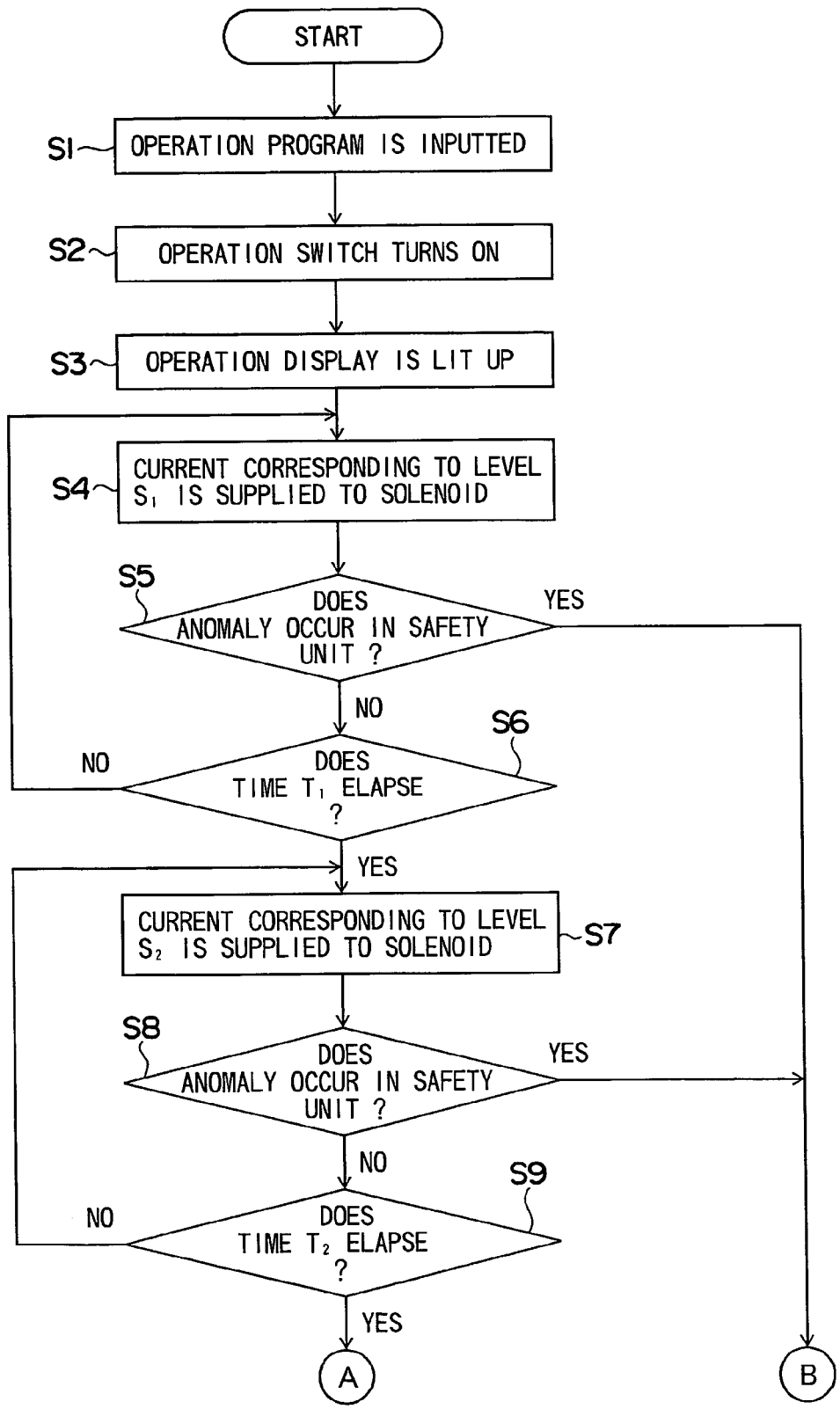
FIG. 7 is a flowchart showing a first half part of a control program.
Figure 8:
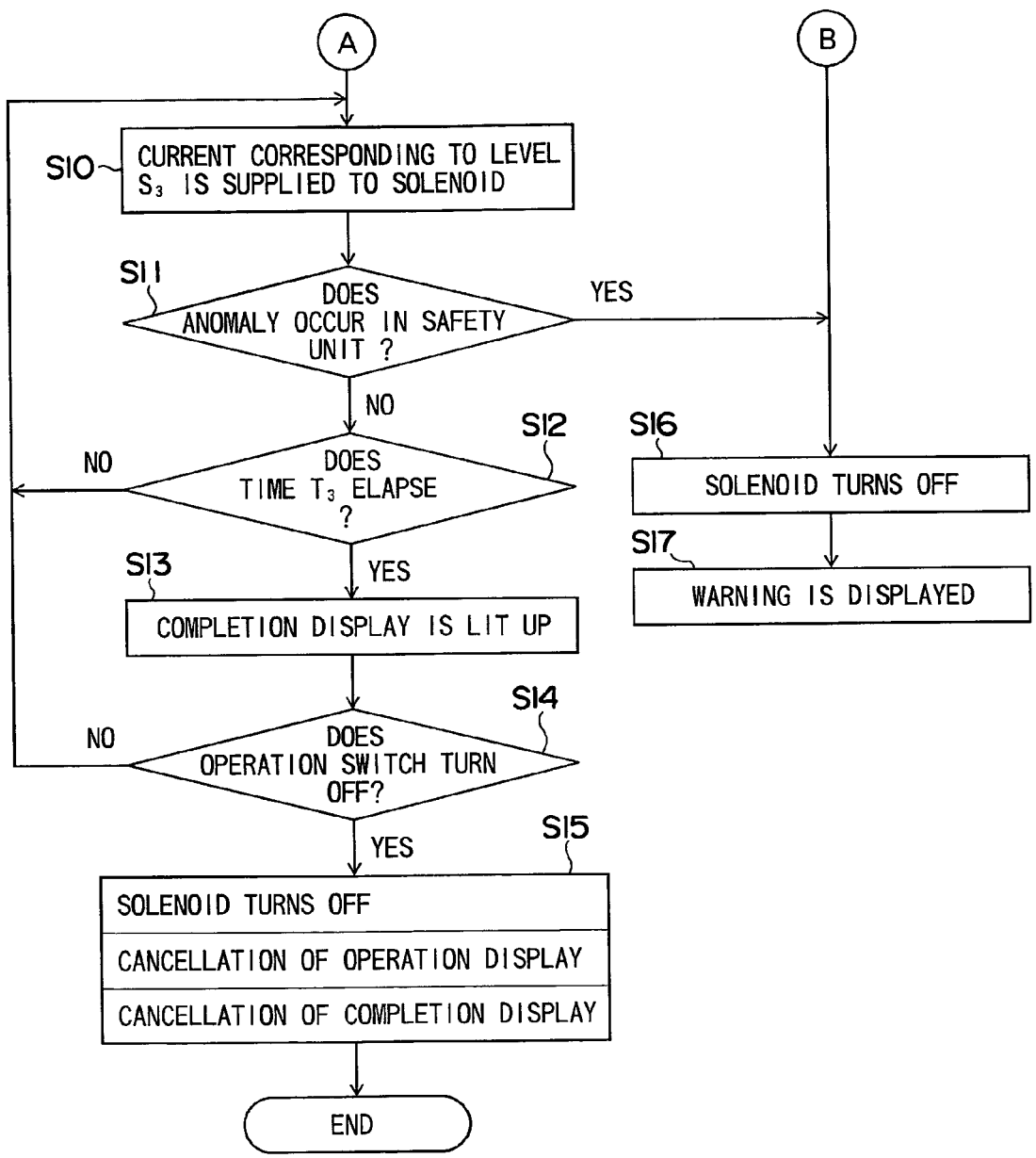
FIG. 8 is a flowchart showing a latter half part of the control program shown in FIG. 7.

A culture processing using the cell/tissue culture apparatus of the first embodiment is next described with reference to flowcharts shown in FIG. 7 and FIG. 8. In FIG. 7 and FIG. 8, depicted by A and B show connecting symbols between the flowcharts.

Upon actual culture, the matrix 32 in which the cell or tissue is transplanted is accommodated in the culture chamber 8 while the cover part 6 is removed, then it is installed in the culture chamber 550. After a temperature, a humidity, a carbon dioxide concentration, an oxygen concentration and so on in the culture chamber are set at proper conditions, a culture fluid 24 having an optimum amount to the cell or tissue is supplied to the matrix 32.

In step S1, the controller 50 is an operation state, and an operation program is inputted through the input unit 502 and a condition setting is effected. Assuming that for input items, first to third stages are set considering the culture stage and so forth, for example, there are set such that a physical stimulation, namely, a level of the tensile stress is $S^1$, its continuation time is $T^1$ in the first stage, a level of the tensile stress is $S^2$, its continuation time is $T^2$ in the second stage, a level of the tensile stress is $S^3$, and its continuation time is $T^3$ in the third stage, the magnitude relation therebetween is established as $S^1 < S^2 < S^3$, $T^1 < T^2 < T^3$. This relation is one example, and hence various conditions can be set.

After setting such conditions, when the operation switch 506 turns ON in step S2, the program goes to step S3 where an operation display is effected on the display part 504 and the display lump 508 is lit up.

In step S4, a current corresponding to the level S1 is supplied to the solenoid 46 so as to cause the tensile stress of a level $S^1$ to act on the culture sheet 22, then the program goes to step S5. In step S5, it is decided whether the anomaly occurs or not in the safety unit 516 so as to maintain the accuracy of tensile stress. In this case, it is decided whether a value of detected current flowing to the solenoid 46 is anomalous level or not and the detected temperature of the solenoid 46 is anomalous temperature or not, and if there does not occur anomaly, the program goes to step S6. In step S6, it is decided whether the continuation time $T^1$ elapses or not, and the processings of the steps S4 and S5 are executed until the continuation time $T^1$ elapses.

Upon elapse of the time $T^1$, the program goes to step S7 where a current corresponding to a level $S^2$ is applied to the solenoid 46, then the program goes to step S8. In step S8, it is decided whether there is anomaly or not in the safety unit 516, and if there is no anomaly, the program goes to step S9. In step S9, it is decided whether time $T^2$ elapses or not, and the processings of steps S7 and S8 are executed until continuation time $T^2$ elapses.

Upon elapse of the time $T^2$, the program goes to step S10 where a current corresponding to the level $S^3$ is applied to the solenoid 46, then the program goes to step S11. In step S11, it is decided whether there is anomaly or not in the safety unit 516, and if there is no anomaly, the program goes to step S12. In step S12, it is decided whether the time $T^3$ elapses or not, and the processings of steps S10 and S11 are executed until continuation time $T^3$ elapses.

Upon elapse of the time $T^3$, the program goes to step S13 where a completion display is effected, then the program goes to step S14 where it is decided whether the operation switch 506 turns OFF or not, and the processings of steps S10 to S13 are executed until the operation switch 506 turns OFF.

When the operation switch 506 turns OFF, the program goes to step S15 where stoppage of the excitation of the solenoid 46, and the cancellation of the operation display and completion display are effected, thereby completing the culture program.

If anomaly turns up in the safety unit 516 in step S5, and step S8 or step S11, the program goes to step S16 where the supply of current to the solenoid 46 is stopped, then the program goes to step S17 where the alarm display is effected on the display part 504, then the alarm buzzer 510 is sounded to notify the anomaly.

Figure 9:
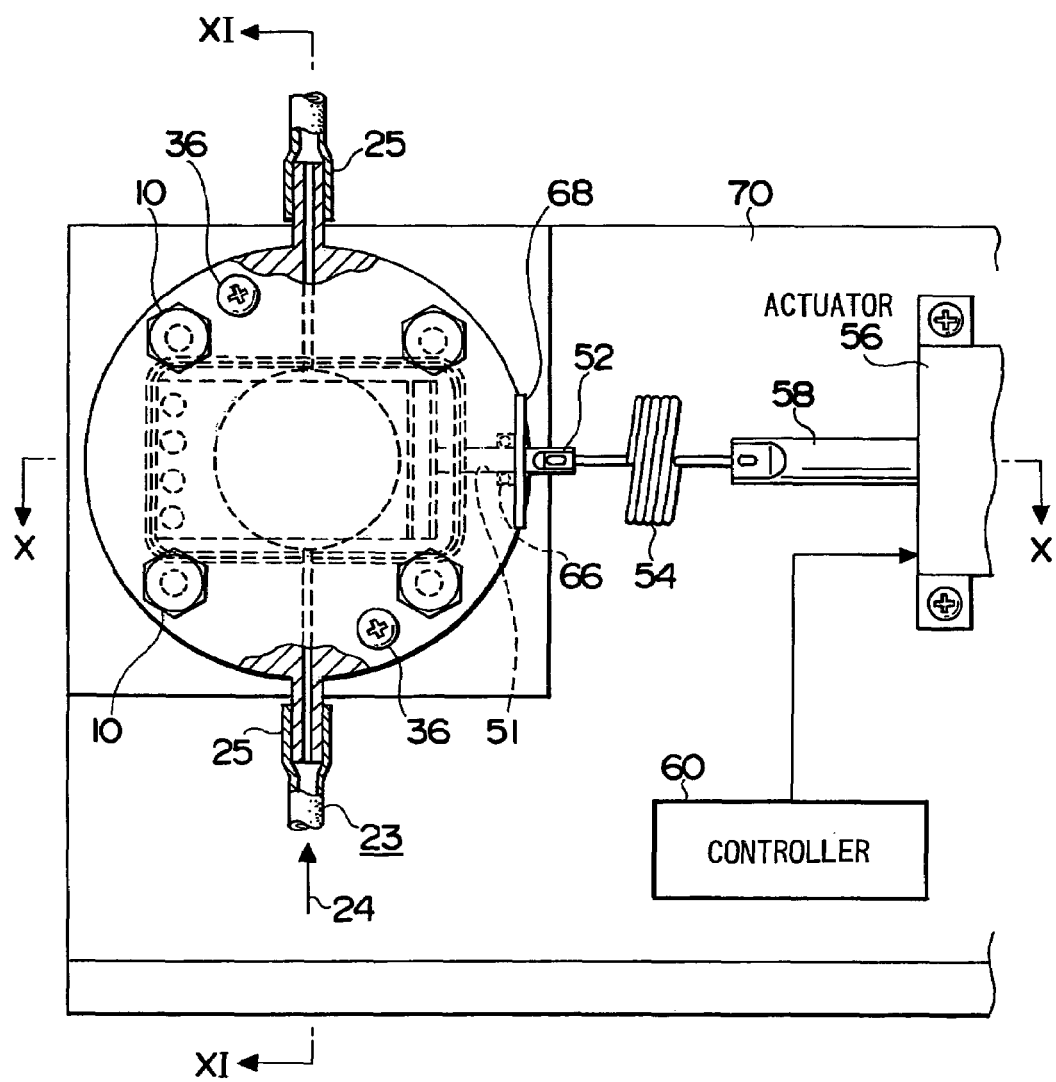
FIG. 9 is a partial front view of a second embodiment of a cell/tissue culture apparatus according to the present invention.
Figure 10:
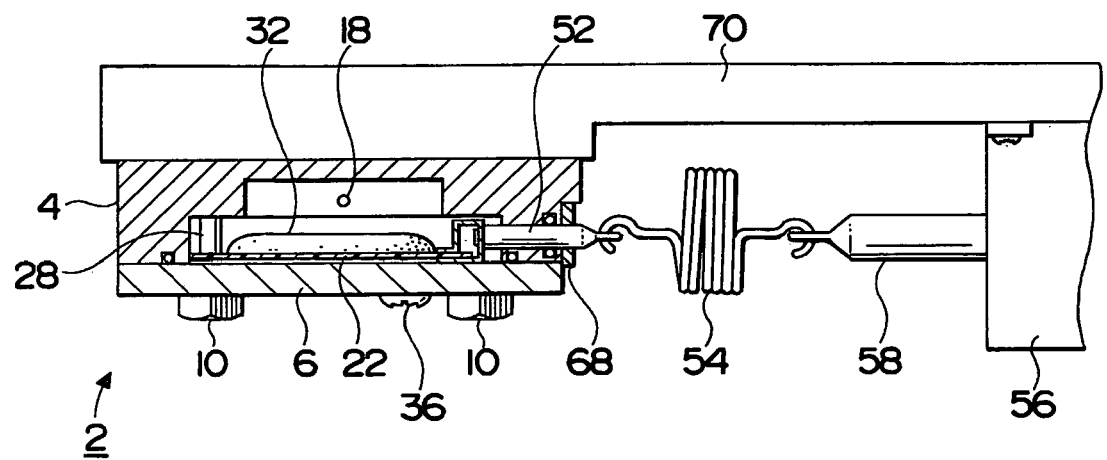
FIG. 10 is a sectional view taken along the line X-X in FIG. 9.
Figure 11:
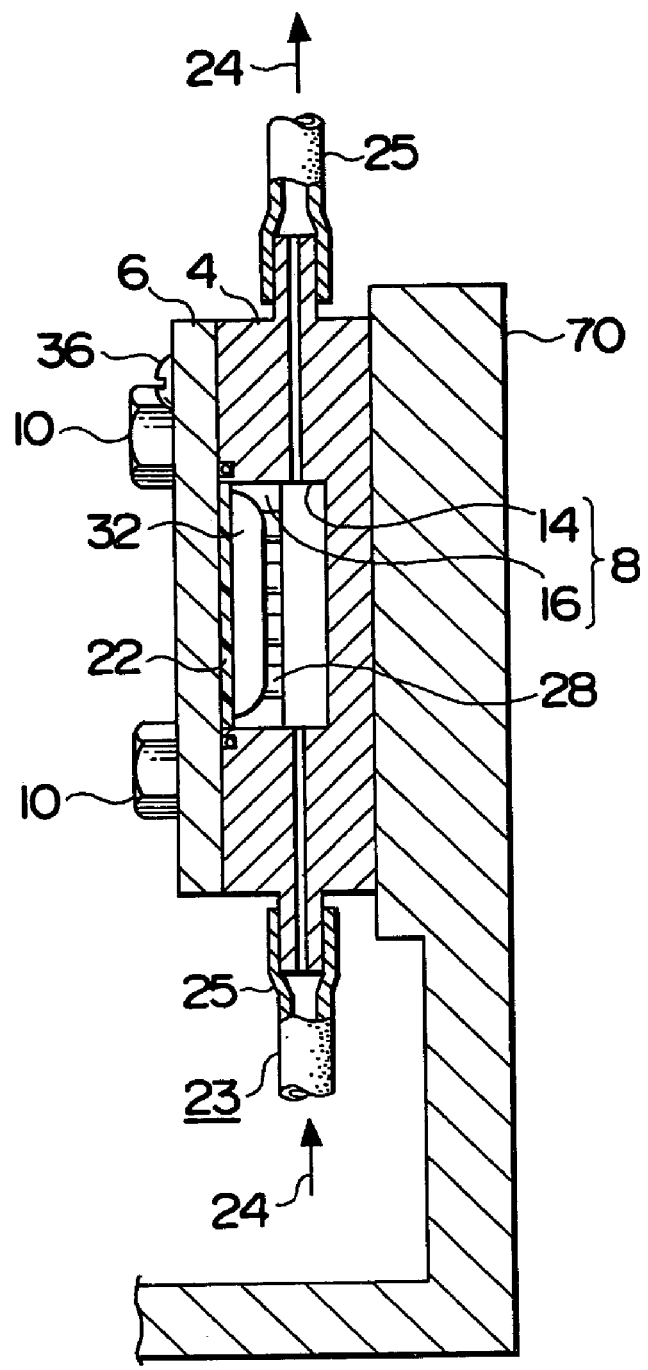
FIG. 11 is a sectional view taken along the line XI-XI in FIG. 9.
Figure 12:
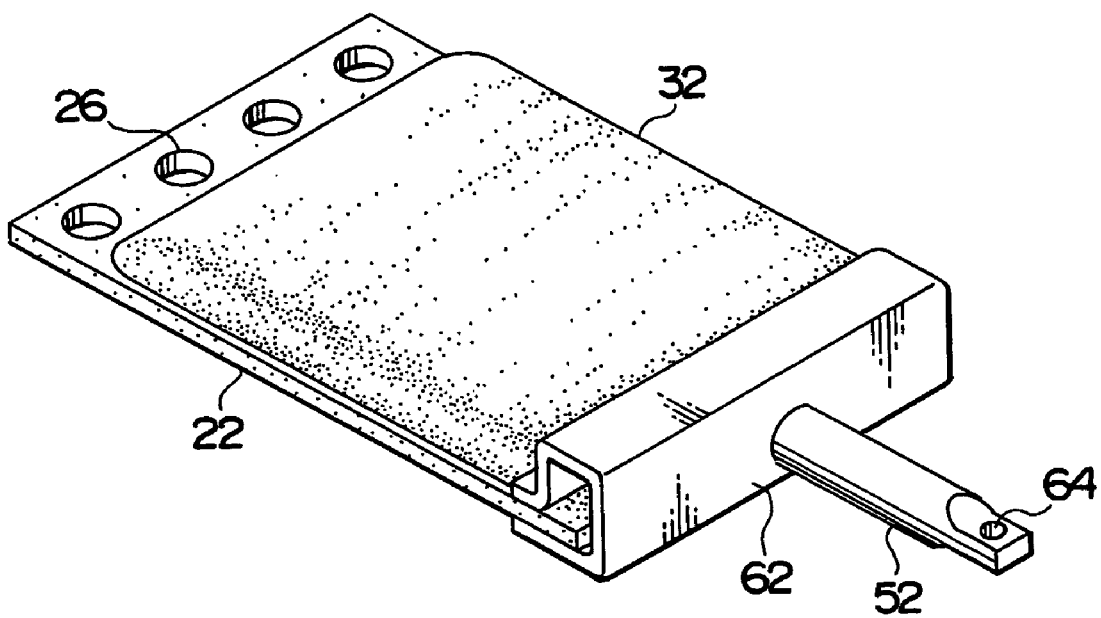
FIG. 12 is a perspective view showing a culture sheet.
Figure 13:
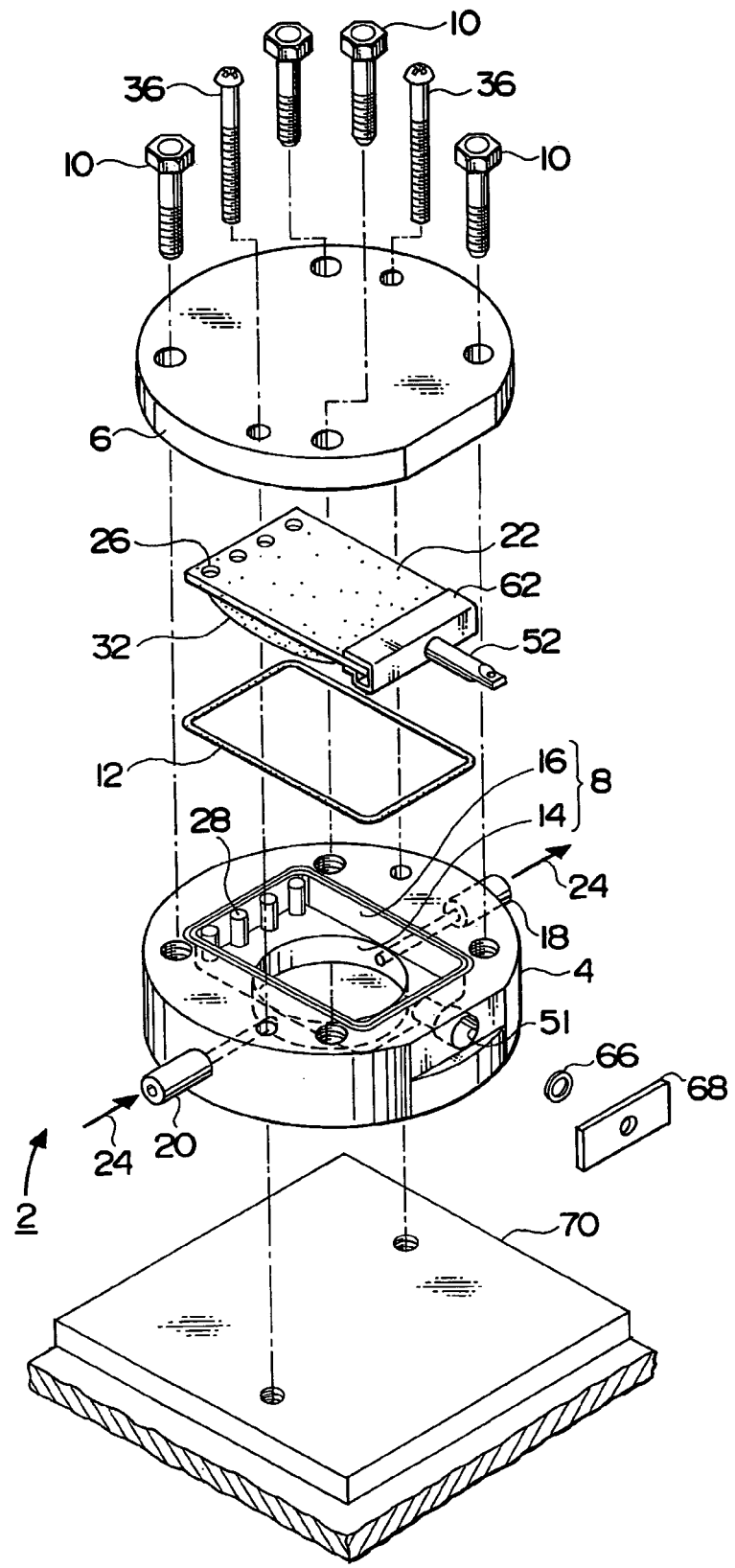
FIG. 13 is an exploded perspective view of a culture unit.
Figure 14:
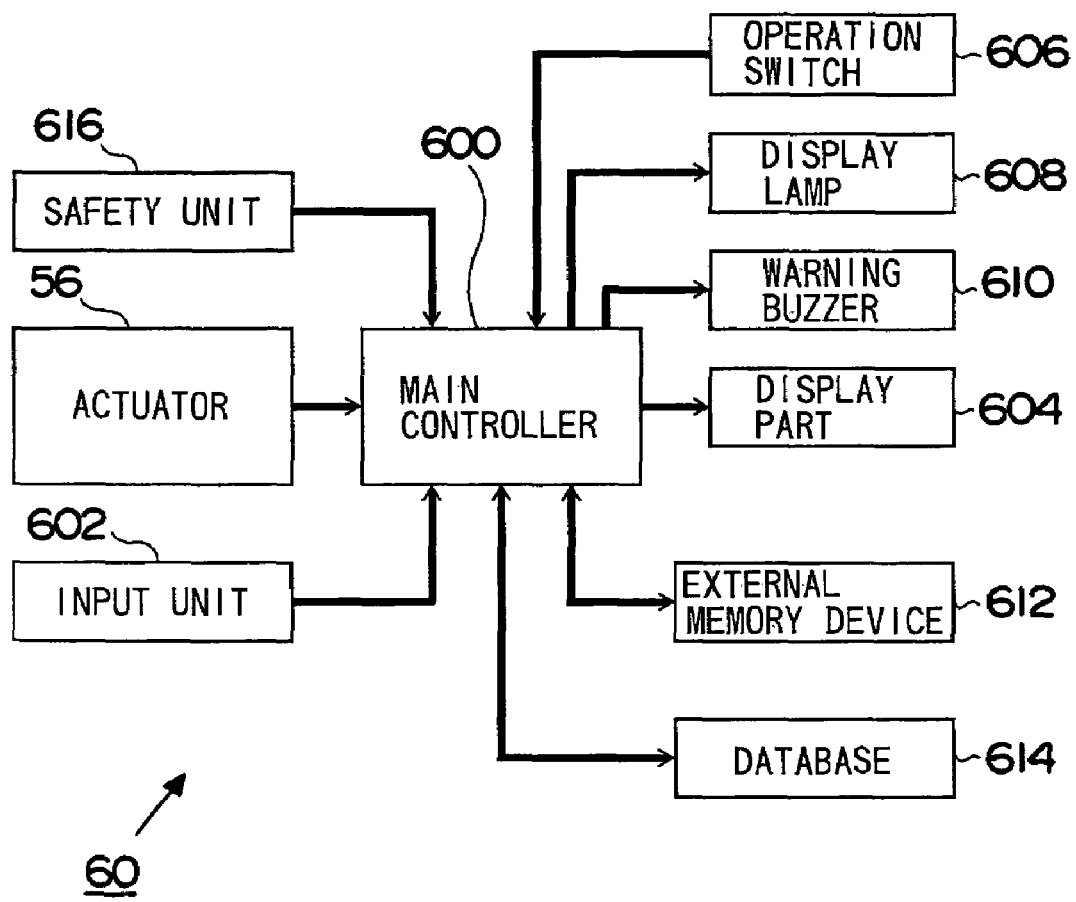
FIG. 14 is a block diagram showing a controller.

Next, FIG. 9 to FIG. 14 show a second embodiment of a cell/tissue culture apparatus, wherein FIG. 9 shows configurations of a culture unit and a driving part, FIG. 10 is a sectional view taken along the line X-X in FIG. 9, FIG. 11 is a sectional view taken along the line XI-XI in FIG. 9, FIG. 12 shows a culture sheet, FIG. 13 shows a culture unit, FIG. 14 shows a configuration of a controller, wherein the constituents which are the same as those in the first embodiment are depicted by the same reference numerals.

According to the cell/tissue culture apparatus of the embodiment, a stress from an outside of a culture chamber 8 is caused to directly act on a culture sheet 22 and a matrix 32 instead of the solenoid 46 in the first embodiment. In this case, a tension spindle 52 attached to the culture sheet 22 is drawn out from a through hole 51 formed in a side wall side of a culture unit 2, and a driving shaft 58 of an actuator 56 serving as stress generating means is attached to one end of the tension spindle 52 via a tension control spring 54. A controller 60 serving as control means for controlling the back and forth movement of the driving shaft 58 is connected to the actuator 56.

As shown in FIG. 12, a chuck 62 serving as fixing means is attached to a free end side of the culture sheet 22, so that the culture sheet 22 is held like a plate shape, and the tension spindle 52 is attached to a back face side of the chuck 62. A through hole 64 through which the tension control spring 54 is attached is formed in the tension spindle 52.

An O-ring 66 serving as hermeticity holding means between the tension spindle 52 and the culture unit 2 is attached to the through hole 51 formed in the side wall part of a container 4 of the culture unit 2, and a block plate 68 serving as means for holding the O-ring at the culture unit 2 side is attached to the side face part of the culture unit 2. The culture unit 2 is detachably attached to a base table 70 by bolts fixing bolts 36. A controller 60 is provided on the actuator 56, serving as means for controlling the driving of the actuator 56, monitoring the proliferation and growth, and so on.

The controller 60 is configured, for example, as shown in FIG. 14. That is, the controller 60 has a main controller 600 which effects display control and so on as well as drive control of the actuator 56 such as a cylinder and so forth for effecting application and relief of a tensile stress relative to the culture sheet 22 when the actuator 56 moves back and forth, and also executes a program control for setting a tension pattern, and so forth. The main controller 600 is provided with a CPU serving as processing means, a ROM, a RAM, and so forth serving as a memory, and a setting of program such as rotation conditions and so forth is effected from an externally connected input unit 602. The main controller 600 is provided with a display part 604, an operation switch 606 for giving an operation instruction, operation display means, for example, a display lump 608, a warning buzzer 610 serving as warning means, an external memory device 612 serving as means for storing various data, a database 614, and so forth. Further, a safety unit 616 for preventing anomalous operation is provided together in the actuator 56.

In the second embodiment, when the actuator 56 is driven to cause the tension to act on the tension spindle 52, the tension can be applied so as to stretch the matrix 32, which proliferates inside the collagen sponge together with the culture sheet 22 while if the driving is cancelled, the culture sheet 22 is contracted owing to its elasticity, resulting in causing a tensile stress and a recovery force caused by the expansion and contraction of the culture sheet 22 to act on the matrix 32. And the supply and circulation of culture fluid 24 needed for culture is effected through the circulation path 23, thereby enhancing proliferation of the cell or tissue in the same manner as the first embodiment.

Figure 15:
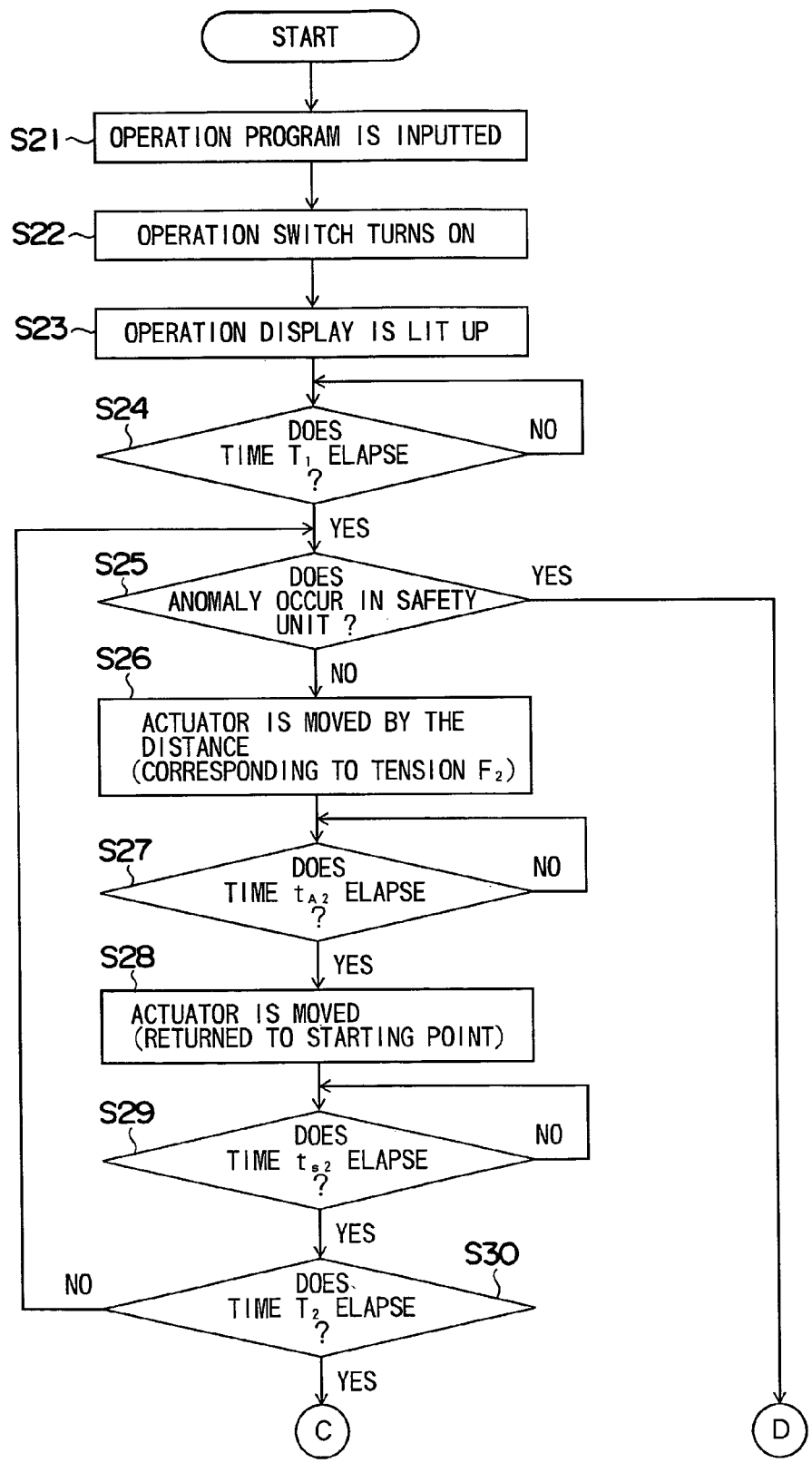
FIG. 15 is a flowchart showing a first half part of a control program.
Figure 16:
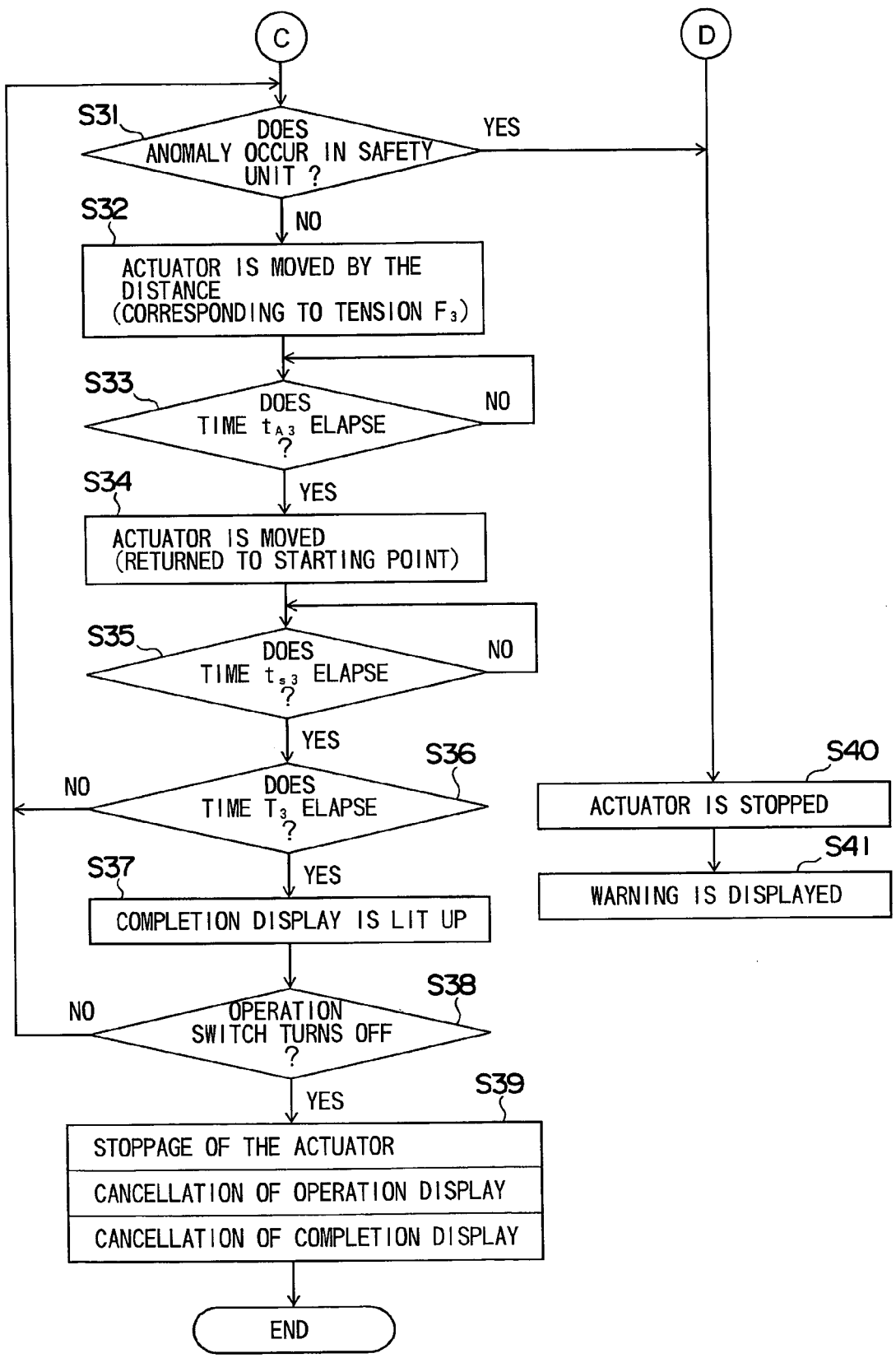
FIG. 16 is a flowchart showing a latter half part of the control program shown in FIG. 15.

A culture processing using the cell/tissue culture apparatus according to the second embodiment is now described with reference to flow charts shown in FIG. 15 and FIG. 16 and a timing chart shown in FIG. 17. In FIG. 15 and FIG. 16, depicted by C and D show connecting symbols between the flowcharts.

Upon actual culture also in the second embodiment, the matrix 32 in which the cell or tissue is transplanted is accommodated in the culture chamber 8 while the cover part 6 is removed, then it is installed in a culture chamber 550. After a temperature, a humidity, a carbon dioxide concentration, an oxygen concentration and so forth in the culture chamber 550 are set at proper conditions, a culture fluid 24 having an amount optimum to the cell or tissue is supplied to the matrix 32, which is the same as the first embodiment.

In step S21, the controller 60 is an operation state, and an operation program is inputted through the input unit 602, thereby effecting a condition setting. Assuming that for input items, first to third stages are set considering the culture stage and so forth, for example, there are set such that continuation time is $T^1$ and a physical stimulation, namely, a tension is $F^1$ ($F^1=0$ in this embodiment) in the first stage, continuation time is $T^2$, a tension is $F^2$, load time is $t^{42}$, non-load time is $t^{S2}$ in the second stage, continuation time is $T^3$, and a tension is $F^3$, load time is $t^{43}$, non-load time is $t^{S3}$ in the third stage, the magnitude relation therebetween is established as $F^1(=0) < F^2 < F^3$, $T^1 < T^2 < T^3$, however, this condition is one example, various conditions can be set.

After setting such conditions, when the operation switch 606 turns ON in step S22, the program goes to step S23 where an operation display is effected on the display part 604 and the display lump 608 is lit up as shown in FIG. 17(A).

In step S24, it is decided whether the time $T^1$ elapses or not, and if the time $T^1$ elapses, the program goes to step S25 where it is decided whether there occurs anomaly or not in the safety unit 616, and if there does not occur anomaly, the program goes to step S26. In step S26, the actuator 56 is moved by the distance corresponding to the tension $F^2$.

In step S27, it is decided whether a load time $t^{42}$ elapses or not. That is, the application of the tension $F^2$ lasts over a period of load time $t^{42}$, and if the load time $t^{42}$ elapses, the program goes to step S28 where the actuator 56 is returned to a starting point, then the program goes to step S29.

In step S29, it is decided whether the non-load time $t^{S2}$ elapses or not, and if the non-load time $t^{S2}$ elapses, the program goes to step S30. In step S30, it is decided whether the continuation time $T^2$ elapses or not, and the processings in Steps S25 to S29 are continuously executed until the continuation time $T^2$ elapses, as shown in FIG. 17(C).

If time $T^3$ elapses, the program goes to step S31 where it is decided whether there occurs anomaly in the safety unit 616 or not, and if there does not occur abnormally, the program goes to step S32. In step S32, the actuator 56 is moved by a distance corresponding to the tension $F^3$, then the program goes to step S33.

Instep S33, it is decided whether the load time $t^{43}$ elapses or not, and a state where the tension $F^3$ is acted continues until the load time $t^{42}$ elapses.

If the load time $t^{43}$ elapses, the program goes to step S34 where the actuator 56 is returned to the starting point, and the program goes to steps S35 where it is decided whether the non-load time $t^{S3}$ elapses or not.

If the non-load time $t^{S3}$ elapses, the program goes to step S36 where the continuation time $T^3$ elapses or not, and the processings in Steps S31 to S35 are continuously executed until the continuation time $T^3$ elapses, as shown in FIG. 17(C).

If time $T^3$ elapses, the program goes to step S37 where completion display is effected, then the program goes to step S38 where it is decided whether the operation switch 606 turns OFF or not, and the completion display is lit up until the operation switch 606 turns OFF, as shown in FIG. 17(B).

When the operation switch 606 turns OFF, the program goes to step S39 where the driving of the actuator 56 is stopped, and the cancellation of the operation display and completion display are effected, thereby completing the culture program.

In the case where the anomaly of the safety unit 616 is turned out in step S25 or step S31, the program goes to step S40 where the driving of the actuator 56 is stopped, then the program goes to step S41 where the occurrence of anomaly is displayed on the display part 604, and the warning buzzer 78 is sounded, thereby notifying the anomaly.

With such processings, a physical stimulation caused by the tension which is differentiated corresponding to each culture stage can be applied to the material to be cultivated in the same manner as the first embodiment. Although a physical stimulation which is constantly varied by the physical exercise, is applied to muscles, tendons, articular cartilage, bones, ligaments and so forth of the human body, with use of the cell/tissue culture apparatus of the second embodiment, it is possible to realize the physical stimulation which is the same as a human body, thereby cultivating a strong cell or tissue. Particularly, according to the second embodiment, since the tension is varied by the acceleration and deceleration, the cell or tissue under the culture realizes a wide range of physical stimulation ranging from pulsative stimulation to gentle stimulation.

Figure 18:
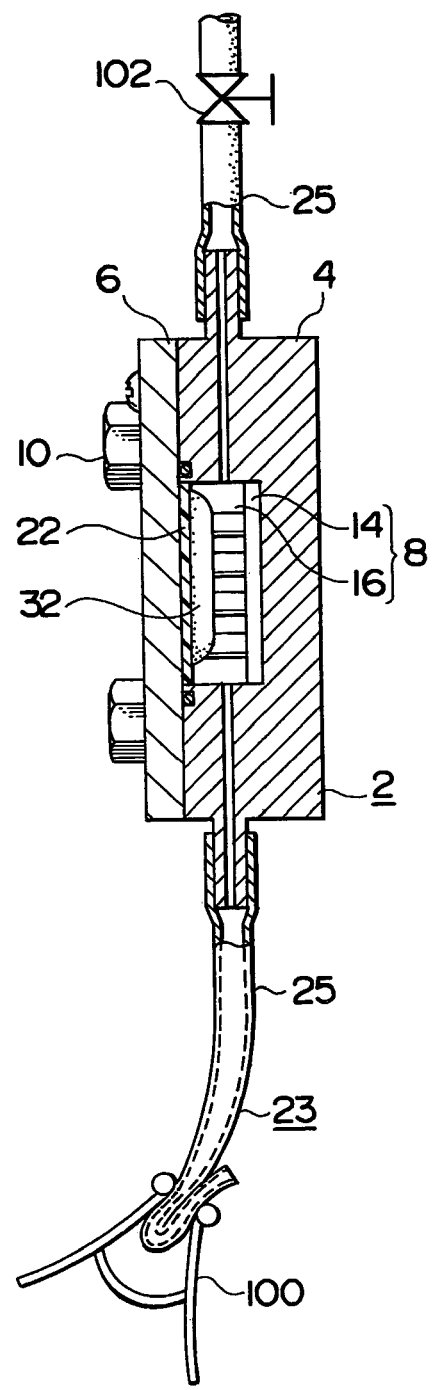
FIG. 18 is a sectional view showing the attachment and detachment of the culture unit.

Next, FIG. 18 shows the attachment and detachment of the culture unit 2. When the culture is terminated using the culture unit 2 as illustrated in the first embodiment or second embodiment, the culture unit 2 shuts, for example, the circulation tube 25 of the circulation path 23 connected to the circulation ports 18, 20, in this example, a pinch cock 100 and a cock valve 102 serving as shutting means are attached to the circulation tube 25 across the culture unit 2, and if a shut processing is effected by the pinch cock 100 and the cock valve 102, the culture unit 2 can be separated from the circulation path 23 and the culture chamber 8 can be held in a hermetically sealed state, thereby preventing the culture fluid 24 from being leaked out.

Further, if the culture unit 2 is sterilized by a sterilizing method using an autoclave, and so forth, UV sterilization, gummer rays sterilization, and so forth, the interior of the culture unit 2 can be maintained in an aseptic condition for a long period of time. According to this embodiment, although the pinch cock 100 and cock valve 102 are employed as means for shutting the circulation tube 25, other shutting means may be employed.

Figure 19:
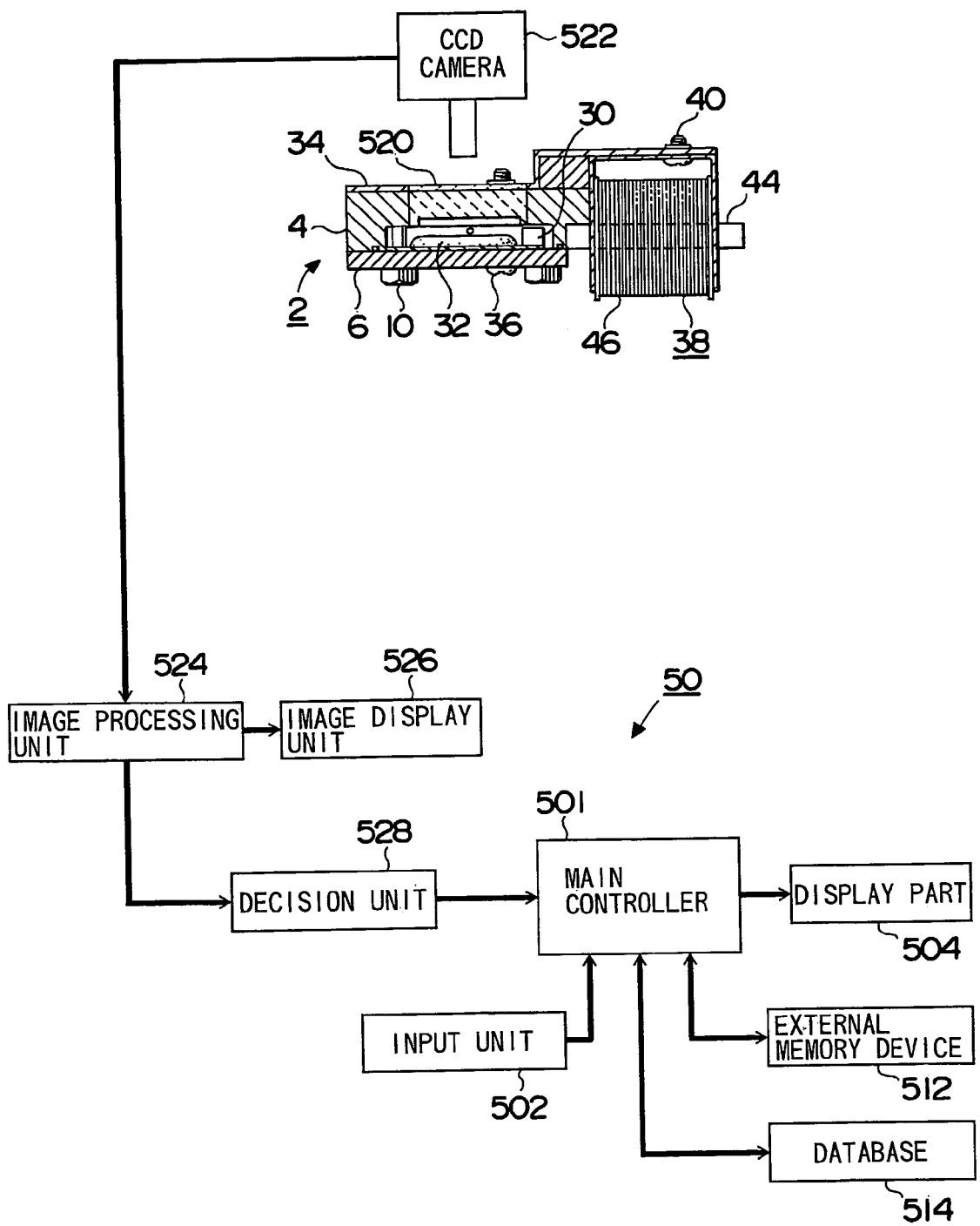
FIG. 19 is a block diagram showing a third embodiment of a cell/tissue culture apparatus according to the present invention.
Figure 22:
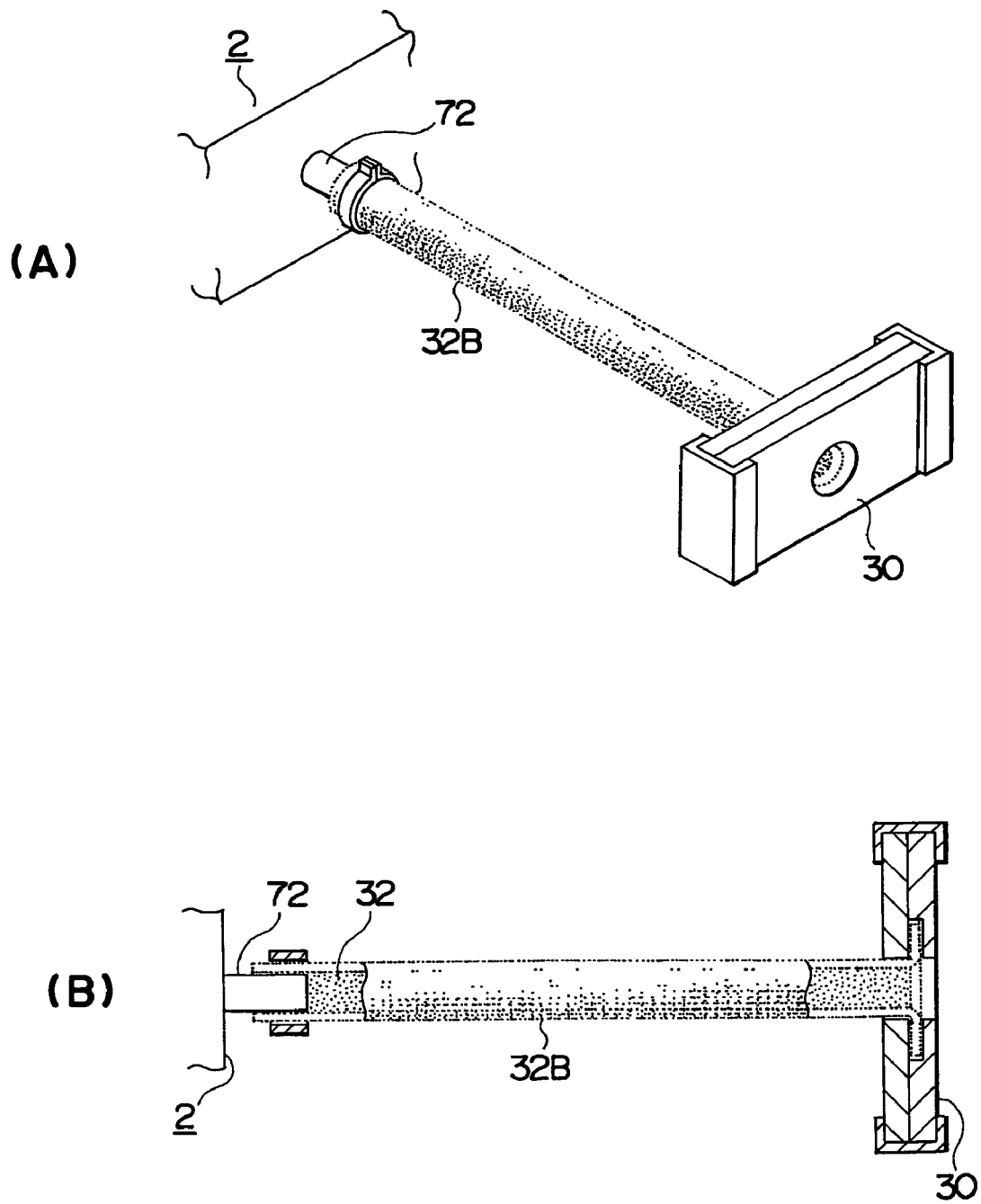
FIG. 22 is a view showing still another embodiment of a material to be cultivated.

Next, FIG. 19 shows a cell/tissue culture apparatus according to a third embodiment of the present invention. According to this embodiment, a seeing through wall part 520 is provided on a base board 34 and a container 4 at a part or as a whole of the culture unit 2 of the first embodiment through which the interior of a culture chamber 8 can be seen, and a CCD camera 522 serving as photographing means for photographing a matrix 32 in the culture chamber 8 is installed in the vicinity of the seeing through wall part 520, wherein image obtained by the CCD camera 522 is supplied to an image processing unit 524 where the image is processed and the processed image is displayed on an image display unit 526, and it is also supplied to a decision unit 528 as decision information. The decision unit 528 decides a proliferation state, growth state of the cell or tissue and proliferation of various bacteria (contamination) in response to the change of color, the shape, and so forth of the matrix 32 based on the processed image, and the result of decision is supplied to a main controller 501. That is, if the state of the matrix 32 in the culture chamber 8 is grasped as image information, and it is observed through this image information, a proliferation state, a growth state or a growth stage of the matrix 32 can be visually grasped with accuracy, and appropriate processing can be executed corresponding to that state. Such a monitor of the interior of the culture unit 2 through seeing can be also applied to the cell/tissue culture apparatus of the second embodiment.

FIGS. 20 to 23 show embodiments of other materials to be cultivated. According to the first embodiment and second embodiment, a culture floor has been formed by use of the culture sheet 22, but as shown in FIG. 20(A), a magnetic body 30 may be attached to a matrix 32 and fixing through holes 26 may be formed on the matrix 32 or as shown in FIG. 20(B), a chuck 62 and a tension spindle 52 may be attached to the matrix 32, and hence a culture sheet 22 is not always required for the material to be cultivated.

Further, as shown in FIG. 21(A), use may be made of a flexible culture body 32A which is formed by weaving a fibrous or string shaped tissue formed of collagen, and so forth serving as a material to be cultivated such as rib stitch, stockinet weaving, and so forth. The through holes 26 may be formed on one fixed end side of the culture body 32A, and a chuck 62 provided with a tension spindle 52 may be attached to a free end side of the culture body 32A, whereby the application and relief of a tension is effected in the same manner. Even with the culture having no culture sheet 22, a sheet-shaped material to be cultivated can be realized as shown in FIG. 21(B). Further, a magnetic body 30 may be attached to a free end side of a culture body 32A in place of the chuck 62 and the tension spindle 52 so as to cause a magnetic to act on force on the magnetic body 30 to apply a stencil stress to the culture body 32A in the same manner as the first embodiment.

As shown in FIG. 22(A) and (B), use is made of a flexibly culture body 32B which is formed by weaving a fibrous or string shaped tissue made of collagen, and so forth serving as a material to be cultivated in a flat sheet, and rolling it in a cylindrical or prismatic shape. In this case, one end of the culture body 32B is fixed to a fixing part 72 which protrudes toward an inner wall part of a culture unit 2, and a magnetic body 30 is attached to the free end side thereof, whereby the application and relief of a tension is repetitively effected by use of an electromagnetic stretcher 38 so as to apply a physical stimulation corresponding to the amount of movement of a body, thereby obtaining a cylindrical or prismatic material to be cultivated. Further, in the case of using such a cylindrical culture body 32B, collagen sponge, and so forth may be filled in the hollow interior of the culture body 32B as a matrix 32.

Further, in the case of using a flexibly culture body 32B which is formed by weaving a fibrous or string shaped tissue made of collagen, and so forth serving as a material to be cultivated in a flat sheet, and rolling in a cylindrical or prismatic shape as shown in FIG. 23(A), one end side of the culture body 32B is fixed by use of a fixing tool 74 which projects toward an inner wall part of a culture unit 2, and a tension spindle 52 is attached to a free end thereof, whereby application and relief of a tension is repetitively effected relative to the culture body 32B by use of the actuator 56 as shown in FIG. 9 and FIG. 10 so as to apply a physical stimulation corresponding to the amount of movement of a human body, thereby obtaining a cylindrical or prismatic material to be cultivated as shown in FIG. 23(B). A collagen sponge, and so forth serving as a matrix 32 may be filled in a hollow part of the cylindrical culture body 32B in the same manner as the previous embodiment.

Figure 17:
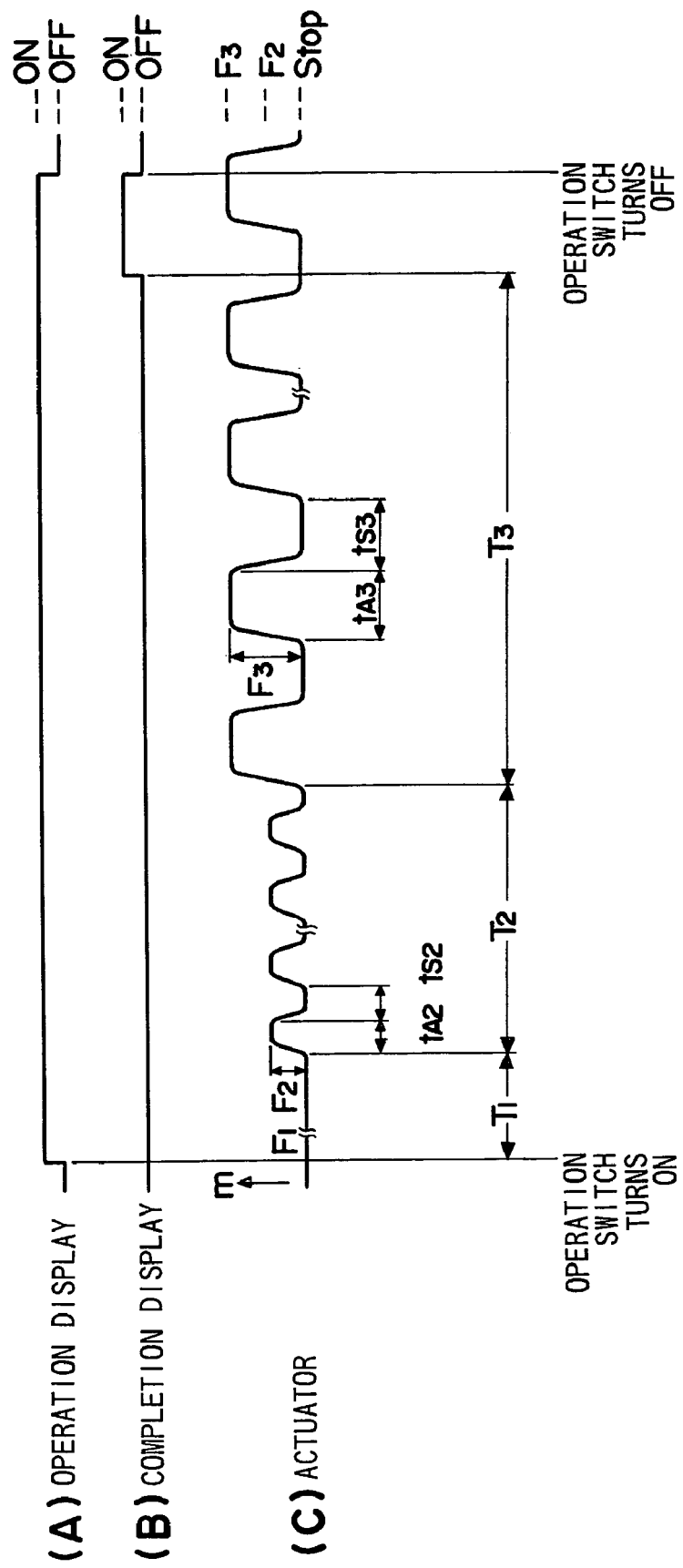
FIG. 17 is a timing chart showing an operation display, completion display and an operation of an actuator.

Incidentally described in the first embodiment is the case where the control as illustrated in the flowcharts of FIG. 7 and FIG. 8 is effected in the cell/tissue culture apparatus, the control as illustrated in FIG. 15 to FIG. 17 may be effected in the cell/tissue culture apparatus of the first embodiment, wherein according to the cell/tissue culture apparatus of the first embodiment, even if there are set, for example, such that continuation time is $T^1$, a physical stimulation, namely, a tension is $F^1(F^1=0$ in this embodiment) in the first stage, continuation time is $T^2$, a tension is $F^2$, load time is $t^{42}$ and non-load time is $t^{S2}$ in the second stage, continuation time is $T^3$ and a tension is $F^3$, load time is $t^{43}$ and non-load time is $t^{S3}$ in the third stage, thereby applying tension change intermittently, the same effect can be expected.

As mentioned in detail above, the following effects can be obtained by the present invention.

a It is possible to apply a physical stimulation such as a tensile stress, and so forth to the material to be cultivated in the chamber in a non-contact state. It is possible to cultivate, for example, a cell or tissue such as tendons, ligaments, and so forth of the living body to which a tensile stress is incessantly applied.

b It is possible to apply a physical stimulation such as a tensile stress, and so forth corresponding to the stage of the growth to the material to be cultivated.

c Since the culture unit accommodating the material to be cultivated therein can be moved by independently separating from the culture circuit, or by detachable from or attaching to the culture circuit, thereby protecting the material to be cultivated from the contamination with various bacteria, and so forth.

d A physical stimulation as desired can be applied to the material to be cultivated, so that a physical stimulation corresponding to the part of a living body can be realized and the acceleration of the culture can be enhanced.

e Each stage of the growth of the cell or tissue can be accurately grasped by image.

Although the configurations, operations and effects of the cell/tissue culture apparatus serving as the mode for carrying out the present invention are described with reference to the embodiments as shown in the attached drawings, the present invention is not limited to such a mode for carrying out the present invention and the embodiments, but it includes all the configurations, which can be predicted or conjectured by a person skilled in the art, such as various configurations, modifications, and so forth which can be conjectured by the object, the mode for carrying out the present invention, and the embodiments of the present invention.

INDUSTRIAL APPLICABILITY

As mentioned above, the cell/tissue culture apparatus of the present invention is useful for the culture of the cell or tissue to which a tissue engineering is applied, more particularly, it is adapted for efficiently realizing a metabolism function of a cell or tissue when performing an in vitro culture of the cell or tissue of a living body such as a human body, and so forth, and for applying a physical stimulation necessary for life prolongation, differentiation, and acceleration of the cell to the material to be cultivated.

The invention claimed is:

1. A cell/tissue culture apparatus comprising:

a culture unit that includes a culture chamber, the culture chamber being formed by installing a cover detachably in a container accommodating a material to be cultivated, the container being openable and closable, wherein the container includes a first part where the material to be cultivated is accommodated and a second part where a culture fluid supplied to the material to be cultivated is introduced and discharged, the culture unit has a fixing member that fixes the container, and the container is hermetically sealed by the cover when the material to be cultivated is cultivated;

a circular port that is formed on a wall part of the second part where the culture fluid of the container is introduced, the circular port allowing the culture fluid to flow into the container and allowing the culture fluid supplied to the material to be cultivated to discharge from the container, the circular port having a first port for introducing the culture fluid from the wall part to the second part and a second port for discharging the culture fluid, which is introduced from the first port into the container, from the second part;

stress generation means that causes a tensile stress from an outside of the chamber to act on the material to be cultivated at one end of the material to be cultivated, the other end of the material to be cultivated being fixed to an interior of the container, the material to be cultivated being held in a direction perpendicular to a flow of the culture fluid flowing in from the circular port, the stress generation means being disposed at the fixing member, where the container is fixed, so as to be located in a direction where the tensile stress for the material to be cultivated acts;

control means that causes the tensile stress generated by the stress generation means to intermit, and causes the tensile stress to undergo gradual increase or gradual decrease in magnitude; and detecting means that detects an anomaly of the stress generation means;

wherein the culture fluid introduced from the circular port to the second part of the container flows into the first part where the material to be cultivated is accommodated, the tensile stress is applied from the stress generation means to the material to be cultivated that receives supply of the culture fluid, the control means makes the tensile stress applied to the material to be cultivated intermit as well as undergo the gradual increase or gradual decrease in magnitude over time to cultivate the material to be cultivated, and in the cultivation, stops the stress generation means when the detecting means detects an anomaly of the stress generation means.

2. A cell/tissue culture apparatus comprising:

a culture unit that includes a culture chamber, the culture chamber being formed by installing a cover detachably in a container accommodating a material to be cultivated, the container being openable and closable, wherein the container includes a first part where the material to be cultivated is accommodated and a second part where a culture fluid supplied to the material to be cultivated is introduced and discharged, the culture unit has a fixing member that fixes the container, and the container is hermetically sealed by the cover when the material to be cultivated is cultivated;

a circular port that is formed on a wall part of the second part where the culture fluid of the container is introduced, the circular port allowing the culture fluid to flow into the container and allowing the culture fluid supplied to the material to be cultivated to discharge from the container, the circular port having a first port for introducing the culture fluid from the wall part to the second part and a second port for discharging the culture fluid, which is introduced from the first port into the container, from the second part;

an elastic member that holds the material to be cultivated expansionably and contractionably, one end of the elastic member being fixed to an interior of the container, the material to be cultivated being held in a direction perpendicular to a flow of the culture fluid flowing in from the circular port;

stress generation means that causes a tensile stress from an outside of the chamber to act on the material to be cultivated at the other end of the elastic member through the intermediary of the elastic member, the stress generation means being disposed at the fixing member, where the container is fixed, so as to be located in a direction where the tensile stress for the material to be cultivated acts;

control means that causes the tensile stress generated by the stress generation means to intermit, and causes the tensile stress to undergo gradual increase or gradual decrease in magnitude; and detecting means that detects an anomaly of the stress generation means;

wherein the culture fluid introduced from the circular port to the second part of the container flows into the first part where the material to be cultivated is accommodated, the tensile stress is applied from the stress generation means through the intermediary of the elastic member to the material to be cultivated that receives supply of the culture fluid, the control means makes the tensile stress applied to the material to be cultivated intermit as well as undergo the gradual increase or gradual decrease in magnitude over time to cultivate the material to be cultivated, and in the cultivation, stops the stress generation means when the detecting means detects an anomaly of the stress generation means.

3. A cell/tissue culture apparatus according to claim 1 or 2, characterized in that the stress generation means is configured by an electromagnetic force generation unit for causing a magnetic force to act on a magnetic body attached to the material to be cultivated or the elastic member.

4. A cell/tissue culture apparatus according to claim 2, characterized in that the elastic member is made of a silicone rubber sheet.

5. A cell/tissue culture apparatus according to claim 1 or 2, characterized in that a culture unit in which the chamber is formed is detachably attachable to a culture circuit for circulating the culture fluid.

6. A cell/tissue culture apparatus according to the claim 1 or 2, characterized in that part or whole of the culture unit in which the chamber is formed and the fixing member is rendered transparent, and provided with photographing means, thereby enabling the material to be cultivated in the chamber to be photographed from an outside of the chamber.

7. A cell/tissue culture apparatus according to claim 1, characterized in that the material to be cultivated is formed in a sheet shape, columnar or prismatic shape.

8. A cell/tissue culture apparatus according to claim 1, characterized in that the material to be cultivated is formed by weaving a fibrous or string shaped tissue and having elasticity.

9. A cell/tissue culture apparatus according to claim 1, characterized in that in the container the first part where the material to be cultivated is accommodated and the second part where the culture fluid supplied to the material to be cultivated is introduced and discharged are differently structured in a shape and/or a volume thereof.

10. A cell/tissue culture apparatus according to claim 2, characterized in that in the container the first part where the material to be cultivated is accommodated and the second part where the culture fluid supplied to the material to be cultivated is introduced and discharged are differently structured in a shape and/or a volume thereof.

11. A cell/tissue culture apparatus comprising:
a culture unit that includes a culture chamber the culture chamber being formed by installing a cover detachably in a container accommodating a material to be cultivated, the container being openable and closable, wherein
the container includes a first part where the material to be cultivated is accommodated and a second part where a culture fluid supplied to the material to be cultivated is introduced and discharged, the culture unit has a fixing member that fixes the container, and the container is hermetically sealed by the cover when the material to be cultivated is cultivated;
a circular port that is formed on a wall part of the second part where the culture fluid of the container is introduced, the circular port allowing the culture fluid to flow into the container and allowing the culture fluid supplied to the material to be cultivated to discharge from the container, the circular port having a first port for introducing the culture fluid from the wall part to the second part and a second port for discharging the culture fluid, which is introduced from the first port into the container, from the second part;
stress generation means that causes a tensile stress from an outside of the chamber to act on the material to be cultivated at one end of the material to be cultivated the other end of the material to be cultivated being fixed to an interior of the container, the material to be cultivated being held in a direction perpendicular to a flow of the culture fluid flowing in from the circular port, the stress generation means being disposed at the fixing member, where the container is fixed, so as to be located in a direction where the tensile stress for the material to be cultivated acts;
control means that causes the tensile stress generated by the stress generation means to intermit, and causes the tensile stress to undergo gradual increase or gradual decrease in magnitude; and
detecting means that detects an anomaly of the stress generation means;
wherein the culture fluid introduced from the circular port to the second part of the container flows into the first part where the material to be cultivated is accommodated, the tensile stress is applied from the stress generation means to the material to be cultivated that receives supply of the culture fluid, the control means makes the tensile stress applied to the material to be cultivated intermit as well as undergo the gradual increase or gradual decrease in magnitude over time to cultivate the material to be cultivated.

12. A cell/tissue culture apparatus according to claim 11, characterized in that in the container the first part where the material to be cultivated is accommodated and the second part where the culture fluid supplied to the material to be cultivated is introduced and discharged are differently structured in a shape and/or a volume thereof.

13. A cell/tissue culture apparatus comprising:
a culture unit that includes a culture chamber, the culture chamber being formed by installing a cover detachably in a container accommodating a material to be cultivated, the container being openable and closable, wherein the container includes a first part where the material to be cultivated is accommodated and a second part where a culture fluid supplied to the material to be cultivated is introduced and discharged, the culture unit has a fixing member that fixes the container, and the container is hermetically sealed by the cover when the material to be cultivated is cultivated;
a circular port that is formed on a wall part of the second part where the culture fluid of the container is introduced, the circular port allowing the culture fluid to flow into the container and allowing the culture fluid supplied to the material to be cultivated to discharge from the container, the circular port having a first port for introducing the culture fluid from the wall part to the second part and a second port for discharging the culture fluid, which is introduced from the first port into the container, from the second part;
an elastic member that holds the material to be cultivated expansionably and contractionably, one end of the elastic member being fixed to an interior of the container, the material to be cultivated being held in a direction perpendicular to a flow of the culture fluid flowing in from the circular port;
stress generation means that causes a tensile stress from an outside of the chamber to act on the material to be cultivated at the other end of the elastic member through the intermediary of the elastic member, the stress generation means being disposed at the fixing member, where the container is fixed, so as to be located in a direction where the tensile stress for the material to be cultivated acts;
control means that causes the tensile stress generated by the stress generation means to intermit, and causes the tensile stress to undergo gradual increase or gradual decrease in magnitude; and
detecting means that detects an anomaly of the stress generation means;
wherein the culture fluid introduced from the circular port to the second part of the container flows into the first part where the material to be cultivated is accommodated, the tensile stress is applied from the stress generation means through the intermediary of the elastic member to the material to be cultivated that receives supply of the culture fluid, the control means makes the tensile stress applied to the material to be cultivated intermit as well as undergo the gradual increase or gradual decrease in magnitude over time to cultivate the material to be cultivated.

14. A cell/tissue culture apparatus according to claim 13, characterized in that in the container the first part where the material to be cultivated is accommodated and the second part where the culture fluid supplied to the material to be cultivated is introduced and discharged are differently structured in a shape and/or a volume thereof.

* * * * *